(12) United States Patent
Khan et al.

(10) Patent No.: US 9,006,472 B2
(45) Date of Patent: Apr. 14, 2015

(54) METHODS FOR THE SYNTHESIS OF 13C LABELED PLASMALOGEN

(71) Applicant: Phenomenome Discoveries Inc., Saskatoon (CA)

(72) Inventors: M. Amin Khan, Morgan Hill, CA (US); Paul L. Wood, Harrogate, TN (US); Dayan Goodenowe, Saskatoon (CA)

(73) Assignee: Phenomenome Discoveries Inc., Saskatoon, Saskatchewan (CA)

( * ) Notice: Subject to any disclaimer, the term of this patent is extended or adjusted under 35 U.S.C. 154(b) by 0 days.

(21) Appl. No.: 14/359,099

(22) PCT Filed: Nov. 16, 2012

(86) PCT No.: PCT/CA2012/001054
§ 371 (c)(1),
(2) Date: May 19, 2014

(87) PCT Pub. No.: WO2013/071412
PCT Pub. Date: May 23, 2013

(65) Prior Publication Data
US 2014/0323749 A1 Oct. 30, 2014

Related U.S. Application Data

(60) Provisional application No. 61/561,212, filed on Nov. 17, 2011, provisional application No. 61/561,219, filed on Nov. 17, 2011, provisional application No. 61/561,225, filed on Nov. 17, 2011.

(51) Int. Cl.
*C07F 9/10* (2006.01)
*C07F 9/6584* (2006.01)
*C07F 7/18* (2006.01)

(52) U.S. Cl.
CPC ............ *C07F 9/10* (2013.01); *C07F 9/65844* (2013.01); *C07F 9/103* (2013.01); *C07F 7/1836* (2013.01)

(58) Field of Classification Search
None
See application file for complete search history.

(56) References Cited

U.S. PATENT DOCUMENTS 5,759,585 A * 6/1998 Forgeot .......................... 424/570
2010/0003761 A1* 1/2010 Cook et al. ...................... 436/71

OTHER PUBLICATIONS

Horton, S.E., et al., Carbon-13 labeling for improved tracer depth profiling of organic materials using secondary ion mass spectrometry, 2006, American Chemical Society for Mass Spectrometry, Short Communication, vol. 17, pp. 1142-1145.*
Sparrow, J.T., et al., Synthesis of carbon-13 labeled tetradecanoic acids, 1983, Journal of Lipid Research, vol. 24, pp. 938-941.*
Yuan, S-S., et al., Synthesis of [1,2,3,4,5-13C5] Palmitic acid, 1984, Journal of labelled compounds and radiopharmaceuticals, vol. XXI, No. 6, pp. 525-532.*
Van Den Bossche et al., "Improved Plasmalogen Synthesis Using Organobarium Intermediates," J. Org. Chem. 72(13):5005-5007 (2007).
International search report and written opinion for corresponding application No. PCT/CA2012/001054, mailed Feb. 14, 2013.
Farooqui et al., "Membrane Phospholipid Alterations in Alzheimer's Disease: Deficiency of Ethanolamine Plasmalogens," Neurochem. Res. 22(4):523-527 (1997).
Office Action for Canadian Patent Application No. 2,812,129 (mailed Aug. 5, 2013).
Office Action for Canadian Patent Application No. 2,812,129 (mailed Nov. 27, 2013).

(Continued)

*Primary Examiner* — Yate K Cutliff
(74) *Attorney, Agent, or Firm* — LeClairRyan, a Professional Corporation

(57) ABSTRACT

A method for preparing $^{13}C$ labeled plasmalogens as represented by Formula B:

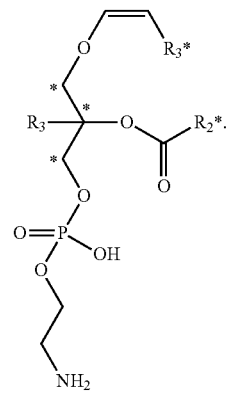

The method involves producing a $^{13}C$ labeled cyclic plasmalogen precursor of Formula A:

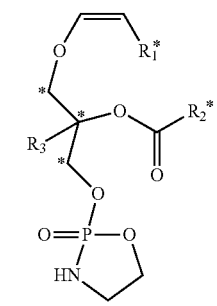

and conversion of the precursor to a plasmalogen of Formula B.

44 Claims, No Drawings

(56) References Cited

OTHER PUBLICATIONS

Gorgas et al., "The Ether Lipid-Deficient Mouse: Tracking Down Plasmalogen Functions," Biochimica et Biophysica Acta 1763:1511-1526 (2006).

Grimm et al., "Plasmalogen Synthesis is Regulated via Alkyl-Dihydroxyacetonephosphate-Synthase by Amyloid Precursor Protein Processing and is Affected in Alzheimer's Disease," J. Neurochem. 116:916-925 (2011).

Shin et al., "Direct Synthesis of Plasmenylcholine from Allyl-Substituted Glycerols," J. Org. Chem. 68:6760-6766 (2003).

Farooqui et al., "Plasmalogens: Workhorse Lipids of Membranes in Normal and Injured Neurons and Glia," Neurosci. 7 (3):232-245 (2001).

Brites et al., "Functions and Biosynthesis of Plasmalogens in Health and Disease," Biochimica et Biophysica Acta 1636:219-231 (2004).

* cited by examiner

METHODS FOR THE SYNTHESIS OF 13C LABELED PLASMALOGEN

This application is a national stage application under 35 U.S.C. §371 of PCT Application No. PCT/CA2012/001054, filed 16 Nov. 2012, which claims the priority benefit of U.S. Provisional Patent Applications Ser. Nos. 61/561,212, 61/561,219, and 61/561,225, each filed 17 Nov. 2011.

FIELD OF INVENTION

The present invention relates to methods for the chemical synthesis of plasmalogens, and specifically, to methods for the chemical synthesis of $^{13}C$ labeled plasmalogens.

BACKGROUND OF THE INVENTION

Plasmalogens are a class of phospholipids characterized by the presence of a vinyl-ether-linked alkyl chain at the sn-1 position, an ester-linked long-chain fatty acid at the sn-2 position, and a head group attached to the sn-3 position through a phosphodiester linkage. They are represented by the following general formula:

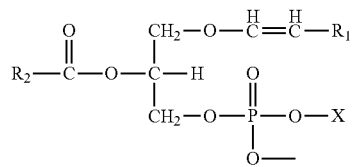

In mammals, the sn-1 position is typically derived from C16:0, C18:0, or C18:1 fatty alcohols while the sn-2 position is most commonly occupied by polyunsaturated fatty acids (PUFAs). The head group can have different identities such as ethanolamine, choline etc.

Plasmalogens are found in numerous human tissues, particularly, in the nervous system, the immune system and the cardiovascular system. They represent one fifth of the total phospholipids in the human body. Plasmalogens are thought to have numerous physiological roles: they are an important structural component of the cell membranes, and act as secondary messengers in cell signaling. In fact, almost 30% of the glycerophospholipids in the adult human brain and up to 70% of myelin sheath ethanolamine glycerophospholipids are plasmalogens. They may also be involved in membrane fusion, ion transport, and cholesterol efflux. Plasmalogens may also act as antioxidants, thus protecting cells from oxidative stress (Plasmalogens: Workhorse Lipids of Membranes in Normal and Injured Neurons and Glia. Akhlaq A. Farooqi, Lloyd A. Horrocks; Neuroscientist. 2001 June; 7(3): 232-45.).

Apart from their normal physiological roles which are still being elucidated, plasmalogens are also implicated in different human diseases (Functions and biosynthesis of plasmalogens in health and diseases, Pedro Brites, Hans R Waterham, Ronald J. A Wanders; Biochim Biophys Acta. 2004 Mar. 22; 1636(2-3):219-31.). In particular, altered levels of tissue plasmalogens has been associated with Zellweger syndrome, rhizomelic chondrodysplasia punctata, Alzheimer's disease, Down syndrome, and Niemann-Pick type C disease etc. (The ether lipid-deficient mouse: tracking down plasmalogen functions. Gorgas K, Teigler A, Komljenovic D, Just W W., Biochim Biophys Acta. 2006 December; 1763(12):1511-26).

A number of reports have been published demonstrating reduced levels of brain plasmalogens in Alzheimer's disease (Plasmalogen synthesis is regulated via alkyl-dihydroxyacetonephosphate-synthase by amyloid precursor protein processing and is affected in Alzheimer's disease, Grimm M O, Kuchenbecker J, Rothhaar T L, Grösgen S, Hundsdorfer B, Burg V K, Friess P, Müller U, Grimm H S, Riemenschneider M, Hartmann T., J Neurochem. 2011 March; 116(5):916-25; Membrane phospholipid alterations in Alzheimer's disease: deficiency of ethanolamine plasmalogens, Farooqui A A, Rapoport S I, Horrocks L A, Neurochem Res. 1997 April; 22(4):523-7.)

The administration of plasmalogens as dietary supplements is now being considered for treatment of Alzheimer's disease.

However, the mechanism of action as well as the fate of plasmalogens in the body is still not completely understood. It is therefore of interest to study the metabolism of plasmalogens in the body. Also, if plasmalogens are to be administered as a dietary supplement, the fate of the plasmalogen supplement administered needs to be known.

Thus stable metabolic tracers for plasmalogens are needed.

Chemical synthesis of plasmalogens can be used to synthesize $^{13}C$ labeled plasmalogens which can be used as metabolic tracers. Several approaches have been tried to chemically synthesize plasmalogens (Direct Synthesis of Plasmenylcholine from Allyl-Substituted Glycerols, Junhwa Shin and David H. Thompson, J. Org. Chem., 2003, 68 (17), pp 6760-6766; Improved to Plasmalogen Synthesis Using Organobarium Intermediates, Jeroen Van den Bossche, Junhwa Shin, s and David H. Thompson, J. Org. Chem., 2007, 72 (13), pp 5005-5007). However, most of the existing chemical synthesis processes face problems due to sensitivity of the vinyl-ether bond to acidic conditions as well as oxidative conditions. Further, there is also a difficulty in generating the Z—O-alkenyl functionality stereoselectively.

SUMMARY OF THE INVENTION

To address these and other problems in the synthesis of labeled plasmalogens, this disclosure aims to provide an improved synthetic method.

In certain embodiments, the chemical synthesis of $^{13}C$ labeled plasmalogens described herein may have improved efficiency over other known methods.

In one aspect of the invention, a process is provided for preparing a compound represented by Formula A

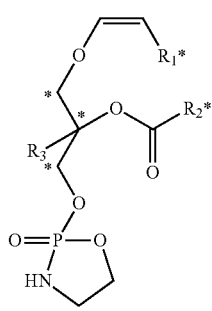

Formula A wherein * represents a $^{13}C$ labeled carbon residue, $R_1$* and $R_2$* are the same or different $^{13}C$ labeled saturated, unsaturated, or polyunsaturated hydrocarbon chains comprising at least one $^{13}C$ labeled carbon atom, and optionally derived from fatty acids; and $R_3$ is hydrogen or a lower alkyl group.

In certain non-limiting embodiments, $R_1^*$, $R_2^*$ or both $R_1^*$ and $R_2^*$ are $C_1$-$C_{28}$ alkyl chains comprising up to 6 double bonds. For instance, without wishing to be limiting, $R_1^*$ can be a $C_1$-$C_{20}$ alkyl group, more preferably a $C_{14}$ alkyl group. In other non-limiting embodiments, $R_2^*$ is a $C_1$-$C_{28}$ alkenyl group, more preferably a $C_{21}$ alkenyl group with 1 to 6 double bonds. In further non-limiting embodiments, $R_3$ is a $C_1$-$C_3$ alkyl group, such as but not limited to methyl, ethyl and propyl.

In this process, the diol present in $^{13}C$ labeled glycerol of Formula 1:

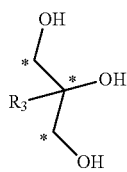

Formula 1 wherein $R_3$ is as defined above, is protected as an acetonide by reaction with dimethoxypropane in the presence of p-toluenesulfonic acid (PTSA) to produce a solketal represented by the compound of Formula 2:

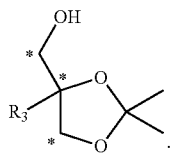

Formula 2

In certain non-limiting embodiments, the compound of Formula 2 is obtained with a yield of about 78%.

The primary alcohol in the compound of Formula 2 is then coupled with an allyl halide, such as but not limited to allyl bromide, to produce a compound as represented by Formula 3:

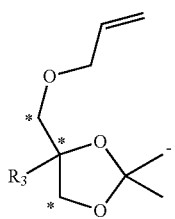

Formula 3

In certain non-limiting embodiments, the compound of Formula 3 is obtained with a yield of about 89%.

The ketal group present in the compound represented by Formula 3 is then deprotected using acidic conditions to produce a compound as represented by Formula 4:

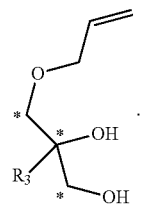

Formula 4

The diol present in the compound represented by Formula 4 is then protected to produce a compound as represented by Formula (v):

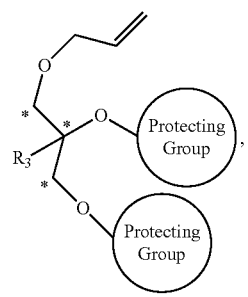

Formula (v)

for instance, but without limiting, to embodiments whereby one or both of the diols are protected with a tert-butyldimethylsilyl (TBS) group to obtain a compound of Formula 5:

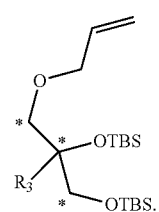

Formula 5

In certain non-limiting embodiments, the compound of Formula 5 is obtained with a yield of about 71%.

$^{13}C$ labeled haloalkane ($XR_1^*$) is then reacted with the compound represented by Formula (v) to produce a compound as represented by Formula (vi):

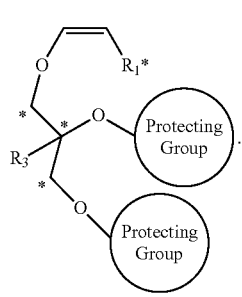

Formula (vi)

wherein $R_1^*$ is as defined above and X is a halogen. In an embodiment, yet without wishing to be limiting, the compound of Formula 5 can be used to obtain the compound of Formula 6:

Formula 6

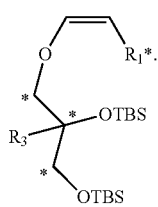

In non-limiting embodiments, X in $XR_1^*$ can be Cl, Br, F or I. In addition, the compound of Formula 6 can, in non-limiting embodiments, be obtained with a yield of up to or about 33%. The ether groups present in the compound represented by Formula (vi) or Formula 6 are deprotected to produce a compound as represented by Formula 7:

Formula 7

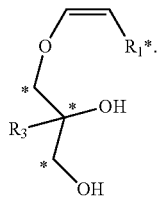

In certain non-limiting embodiments, the compound of Formula 7 is obtained with a yield of up to or about 73%.

The primary alcohol present in the compound represented by Formula 7 is protected to produce a compound as represented by Formula (viii):

Formula (viii)

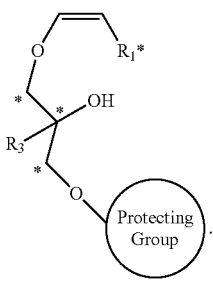

For instance, but without being limiting, the primary diol can be protected with a tert-butyldimethylsilyl (TBS) group to obtain a compound of Formula 8:

Formula 8

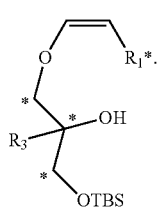

In certain non-limiting embodiments, the compound of Formula 8 is obtained with a yield of up to or about 55%.

$^{13}C$ labeled fatty acid ($R_2^*$—COOH) is esterified at the sn2 position of the compound represented by Formula (viii), such as but not limited to the compound of Formula 8, to produce a compound represented by Formula (ix):

Formula (ix)

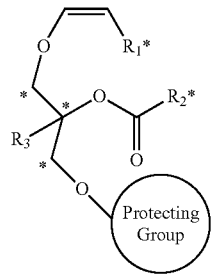

Wherein $R_2^*$ is as defined above. In an embodiment, yet without wishing to be limiting, the compound of Formula 8 can be used to obtain the compound of Formula 9:

Formula 9

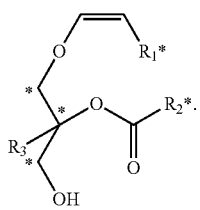

In certain non-limiting embodiments, the compound of Formula 9 is obtained with a yield of up to or about 77%.

The ether present in the compound represented by Formula (ix) or, in certain embodiments the compound of Formula 9, is then deprotected to produce a compound as represented by Formula 10:

Formula 10

In certain non-limiting embodiments, the compound of Formula 10 is obtained with a yield of up to or about 59%.

Finally, the compound represented by Formula 10 is reacted with $POCL_3$, $Et_3N$ and ethanolamine to yield the compound represented by Formula A. In certain non-limiting embodiments, the compound of Formula A is obtained with a yield of up to or about 44%.

In a preferred embodiment, the $^{13}C$ labeled fatty acid ($R_2^*$—COOH) is $^{13}C$ labeled docosahexaenoic acid (DHA).

In yet another preferred embodiment, the $^{13}C$ labeled haloalkane ($XR_1^*$) is $^{13}C$ labeled iodotridecane.

In yet another preferred embodiment, the protection reactions to produce the compounds represented by Formula 5 and Formula 8 are carried with tert-butyldimethylsilyl chloride (TBDMSCl).

In yet another preferred embodiment, the deprotection reactions to produce the compounds represented by Formula 7 and Formula 10 are carried out in the presence of tetrahydrofuran (THF) and tetra-n-butylammonium fluoride (TBAF).

In yet another preferred embodiment, the $^{13}C$ labeled fatty acid ($R_2^*$—COOH) is $^{13}C$ labeled DHA, and the $^{13}C$ labeled haloalkane (XR$_1$*) is $^{13}$C labeled iodotridecane, and the compound produced is as represented in Formula A':

Formula A'

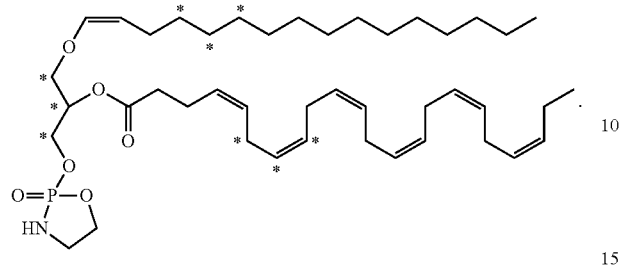

In another aspect of the invention, a process is provided for preparing a compound as represented by Formula B:

Formula B

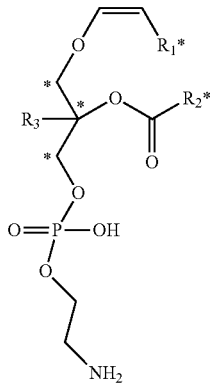

wherein * represents a $^{13}$C labeled carbon residue, and R$_1$*, R$_2$* and R$_3$ are all as described above.

In this process, the compound of Formula A is converted to a compound of Formula B in the presence of water and tetrahydrofuran (THF).

In certain embodiments, the compound of Formula A may be prepared according to methods as described above. In addition, according to a preferred embodiment, the compound of Formula A' as described above may accordingly be converted to a compound as represented by Formula B':

Formula B'

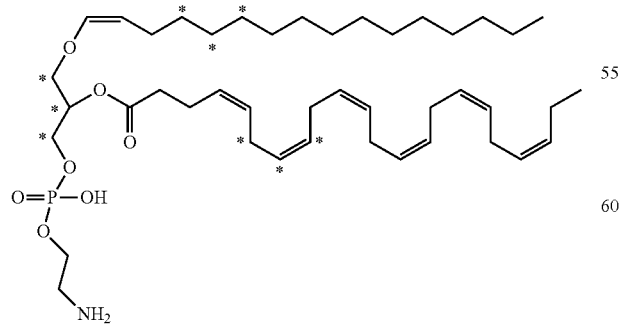

by the above process.

DETAILED DESCRIPTION

The present invention provides cyclic precursors useful in the synthesis of $^{13}$C labeled plasmalogens, the precursor being represented by compounds of Formula A:

Formula A

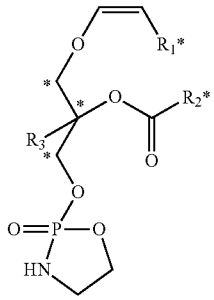

wherein * represents a $^{13}$C labeled carbon atom,
R$_1$* and R$_2$* are the same or different $^{13}$C labeled saturated, unsaturated, or polyunsaturated hydrocarbon chains comprising at least one $^{13}$C labeled carbon atom, and optionally derived from fatty acids; and R$_3$ is hydrogen or a lower alkyl group.

In certain non-limiting embodiments, R$_1$*, R$_2$* or both R$_1$* and R$_2$* are C$_1$-C$_{28}$ alkyl chains comprising up to 6 double bonds. For instance, without wishing to be limiting, R$_1$* can be a C$_1$-C$_{20}$ alkyl group, more preferably a C$_{14}$ alkyl group. In other non-limiting embodiments, R$_2$* is a C$_1$-C$_{28}$ alkenyl group, more preferably a C$_{21}$ alkenyl group with 1 to 6 double bonds. In further non-limiting embodiments, R$_3$ is a C$_1$-C$_3$ alkyl group, such as but not limited to methyl, ethyl and propyl.

The present invention also provides a process for preparing cyclic precursors useful in the synthesis of $^{13}$C labeled plasmalogens, the precursors being represented by compounds of Formula A as described above.

In certain embodiments, yet without wishing to be limiting in any way, these cyclic precursors can provide several advantages for efficient synthesis of plasmalogens. For instance, the polarity and solubility of the cyclic intermediate can increase the ease of purification of the to intermediate. The cyclic intermediate is also, in certain embodiments, stable under both chromatographic conditions and under HPLC conditions; and can be hydrolyzed to produce plasmalogens in aqueous media.

The present invention further provides a process for preparing plasmalogens as represented by compounds of Formula B Formula B

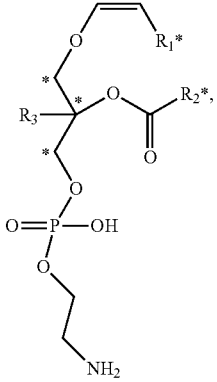

wherein * represents a $^{13}$C labeled carbon atom and $R_1^*$, $R_2^*$ and $R_3$ are as described above, from the cyclic precursors of Formula A described above.

This synthetic route can, in certain preferred embodiments, yield high purity of $^{13}$C plasmalogen, and at reduced cost as compared to other methods through the use of generally abundant and inexpensive reagents. The process also has the advantage that, in certain embodiments, no downstream processing is required. In addition, because a highly pure $^{13}$C plasmalogen product can be obtained in certain non-limiting embodiments of the described process, the relative amount of plasmalogen that is needed in the end application(s) is reduced, which can further reduce costs.

It will be appreciated by those skilled in the art that each of the embodiments of the invention described herein may be utilized individually or combined in one or more manners different than the ones disclosed above for the production of $^{13}$C labeled plasmalogens. In addition, those skilled in the art will be able to select a suitable temperature in view of the reaction conditions being used, in further embodiments of the invention encompassed herein.

The literature referred to herein establishes knowledge that is available to those with skill in the art. Unless otherwise defined, all technical and scientific terms used herein have the same meaning as commonly understood by one of ordinary skill in the art to which this invention relates. All references cited herein are hereby incorporated by reference to the same extent as if each was specifically and individually incorporated by reference.

Although methods and materials similar or equivalent to those described herein can be used in the practice or testing of the present invention, the preferred methods and materials are described herein. In the case of inconsistencies, the present disclosure, including definitions, will control. In addition, the materials, methods, and examples are illustrative only and are not intended to be limiting.

The term "about" is used herein to mean approximately, in the region of, roughly, or around. When the term "about" is used in conjunction with a numerical range, it modifies that range by extending the boundaries above and below the numerical values set forth. The term "comprises" is used herein to mean "includes, but is not limited to."

The following abbreviations are used throughout the specification:
AcOH: Acetic Acid
CuI: Copper Iodide
DCM: Dichloromethane
DHA: Docosahexanoic Acid
DHP: Dihydropyran
DMAP: 4-Dimethylaminopyridine
DMF: Dimethylformamide
EDC: 1-ethyl-3-(3-dimethylaminopropyl) carbodiimide
EDC.HCl: 1-Ethyl-3-(3-dimethyllaminopropyl)carbodiimide hydrochloride
EtOAc: Ethyl Acetate
Et$_3$N: Triethylamine
HCl: Hydrocholoric Acid
HMPA: Hexamethylphosphoramide
Im: Imidazole
K$_2$CO$_3$: Potassium Carbonate
KOH: Potassium Hydroxide
MeOH: Methanol
NaH: Sodium Hydride
NaHCO$_3$: Sodium Carbonate
Na$_2$SO$_4$: Sodium Sulphate
n-BuLi: n-Butyllithium
PBr$_3$: Phosphorus Tribromide
Pd/C: Palladium on Carbon
POCl$_3$: Phosphoryl Chloride
PPh$_3$: Triphenyl Phosphine
PTSA: p-toluenesulfonic acid
Py: Pyrimidine
sec-BuLi: sec-Butyllithium
TBAI: Tetrabutylammonium Iodide
TBAF: Tetra-n-butylammonium fluoride
TBDMSCl: tert-Butyldimethylsilyl chloride
TEA: Triethanolamine
THF: Tetrahydrofuran
THP: Tetrahydropyran
TsCl: Tosyl Chloride In one non-limiting embodiment of the invention, cyclic precursors for plasmalogen synthesis represented by compounds of Formula A are provided:

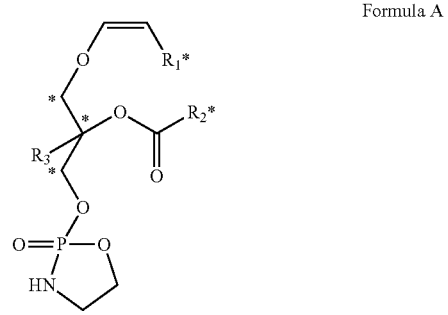

Formula A wherein;
$R_1^*$ and $R_2^*$ are the same or different $^{13}$C labeled saturated, unsaturated, or polyunsaturated hydrocarbon chains comprising at least one $^{13}$C labeled carbon atom, and optionally derived from fatty acids; and $R_3$ is hydrogen or a lower alkyl group.

In certain non-limiting embodiments, $R_1^*$ and $R_2^*$ can be derived from any saturated, unsaturated or polyunsaturated fatty acids or alkyl halides. In a preferred embodiment, $R_1^*$ is derived from $^{13}$C-iodotridecane (including but not limited to that described in U.S. Patent Application No. 61/561,219, incorporated herein by reference), $R_2^*$ is derived from $^{13}$C-docosahexanoic acid (including but not limited to that described in U.S. Patent Application No. 61/561,225, incorporated herein by reference), and $R_3$ is hydrogen such that the compound of Formula A is:

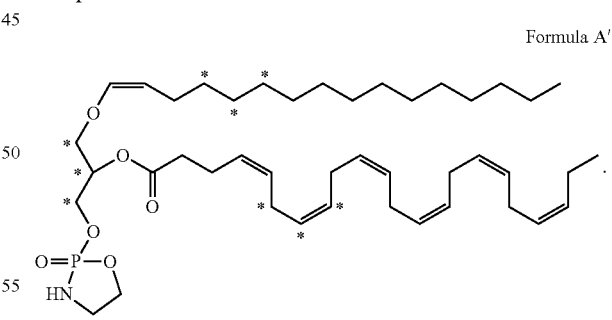

Formula A'

In further embodiments, yet without wishing to be limiting in any way, and in addition to $^{13}$C-iodotridecane, the $^{13}$C labeled alkyl halides may alternately be $^{13}$C-chlorotridecane, $^{13}$C-bromotridecane, or $^{13}$C-fluorotridecane.

In yet further embodiments, the term "lower alkyl group" may refer to $C_{1-3}$ alkyl groups, preferably straight chain alkyl groups such as methyl, ethyl, or propyl.

In another non-limiting embodiment, a 10-step process for preparing cyclic precursors for plasmalogen synthesis, as represented by the compounds of Formula A, is provided. The synthetic process is depicted in Scheme A:

Scheme A

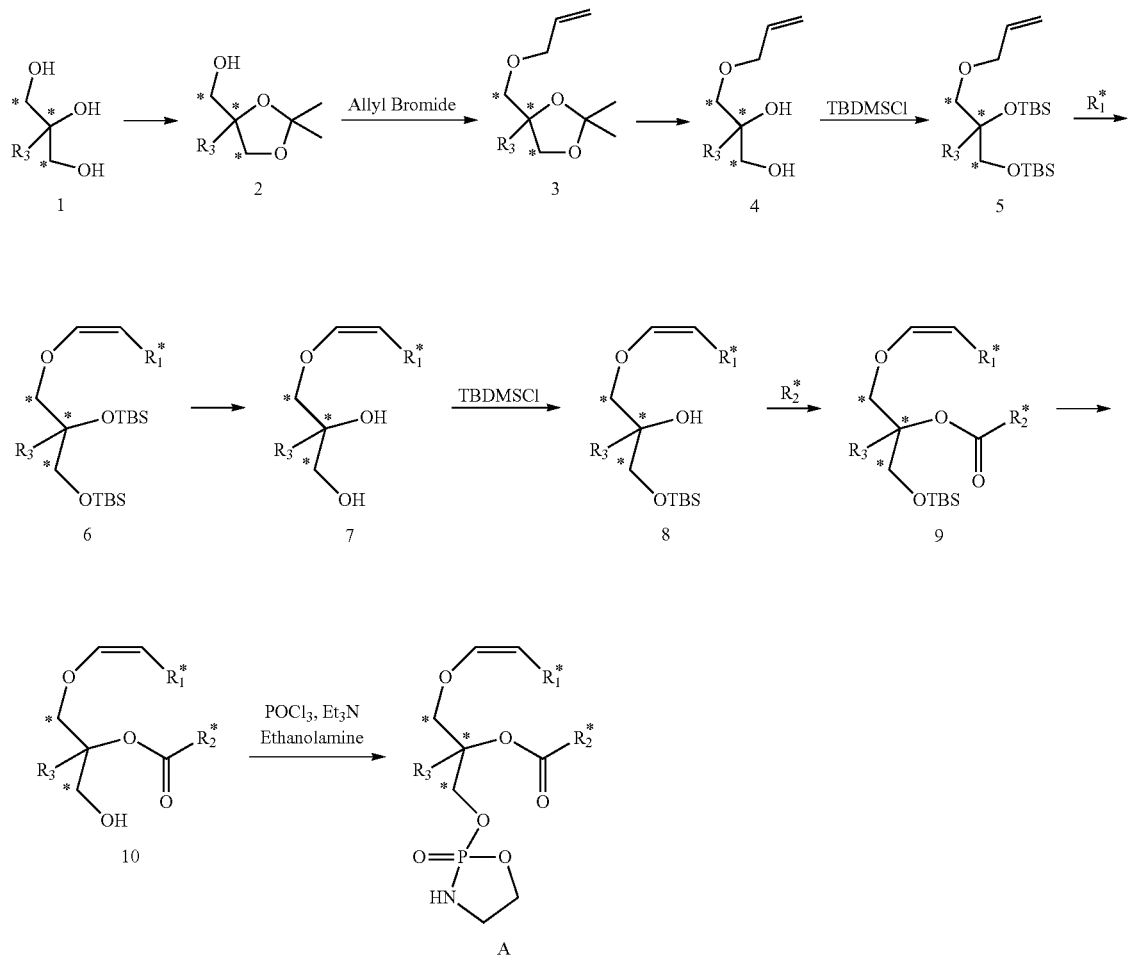

In this synthetic process a $^{13}C$ labeled glycerol is used as starting material to produce the $^{13}C$ labeled plasmalogen. The sequence of steps carried out is as follows: the diol of $^{13}C$ labeled glycerol (Formula 1) is protected as acetonide resulting in production of compound represented by Formula 2. The compound of Formula 2 is coupled with allyl bromide to produce a compound represented by Formula 3. Ketal in the compound represented by Formula 3 is deprotected to obtain a compound represented by Formula 4. Diol of the compound represented by Formula 4 is protected as a TBDMS ether to obtain a compound as represented by Formula 5. The compound represented by Formula 5 is reacted with $^{13}C$ labeled haloalkane ($XR_1^*$) in the presence of sec-BuLi to produce a compound as represented by Formula 6. The compound thus obtained was deprotected of TDBMS ether to produce a compound of Formula 7. Primary alcohol present in the compound represented by Formula 7 is protected with TDBMS to obtain a compound as represented by Formula 8. $^{13}C$ labeled fatty acid ($R_2^*$—COOH) is esterified at the sn2 position of the compound represented by Formula 8 in the presence of EDC.HCL/DMAP to produce a compound represented by Formula 9. Compound represented by Formula 9 is deprotected in the presence of AcOH to produce a compound as represented by Formula 10. A cyclic phosphoethanolamine group is added to the compound represented by Formula 10 to produce a compound as represented by Formula A, using a two step protocol, wherein $POCl_3$ is added to the compound represented by Formula 10 to produce a dichlorophosphate intermediate, which is quenched with ethanolamine to give the cyclic phosphoethanolamine.

In another embodiment, a process is provided for preparing $^{13}C$ labeled plasmalogens as represented by the compounds of Formula B described herein, using the cyclic precursors as represented by the compounds of Formula A described herein. This process is depicted in Scheme B:

Scheme B

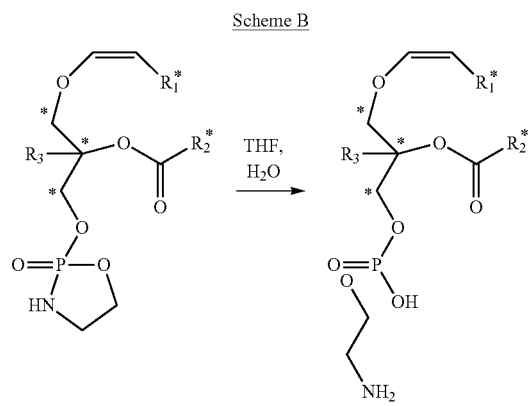

In a preferred yet non-limiting embodiment, $R_1^*$ is derived from $^{13}C$-iodotridecane, $R_2^*$ is derived from $^{13}C$-docosahexanoic acid and $R_3$ is hydrogen, such that the compound of Formula B produced is as represented by Formula B':

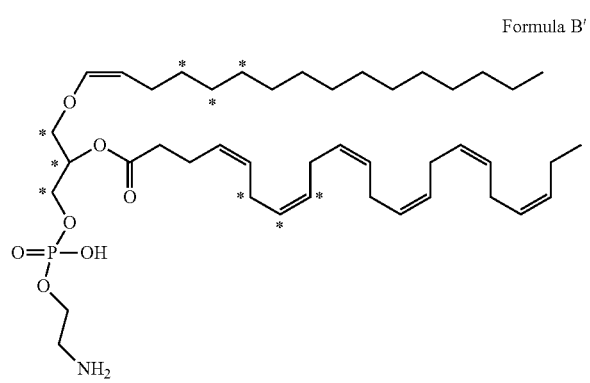 [SMILES: CC/C=C\C/C=C\C/C=C\C/C=C\C/C=C\C/C=C\CCC(=O)OC(CO/C=C\CCCCCCCCCCCCCC)COP(=O)(O)OCCN]

by the above process.

This conversion of the cyclic plasmalogen precursor of Formula A to the plasmalogen of Formula B is a single step process and can be carried out in aqueous media.

EXAMPLES

The following provides examples of certain preferred embodiments of the synthetic processes described herein for producing the $^{13}C$ labeled cyclic plasmalogen precursor of Formula A, and the plasmalogen of Formula B.

A non-limiting example of a process for production of the cyclic plasmalogen precursor Formula A in accordance with a preferred embodiment of the invention is depicted in Scheme C:

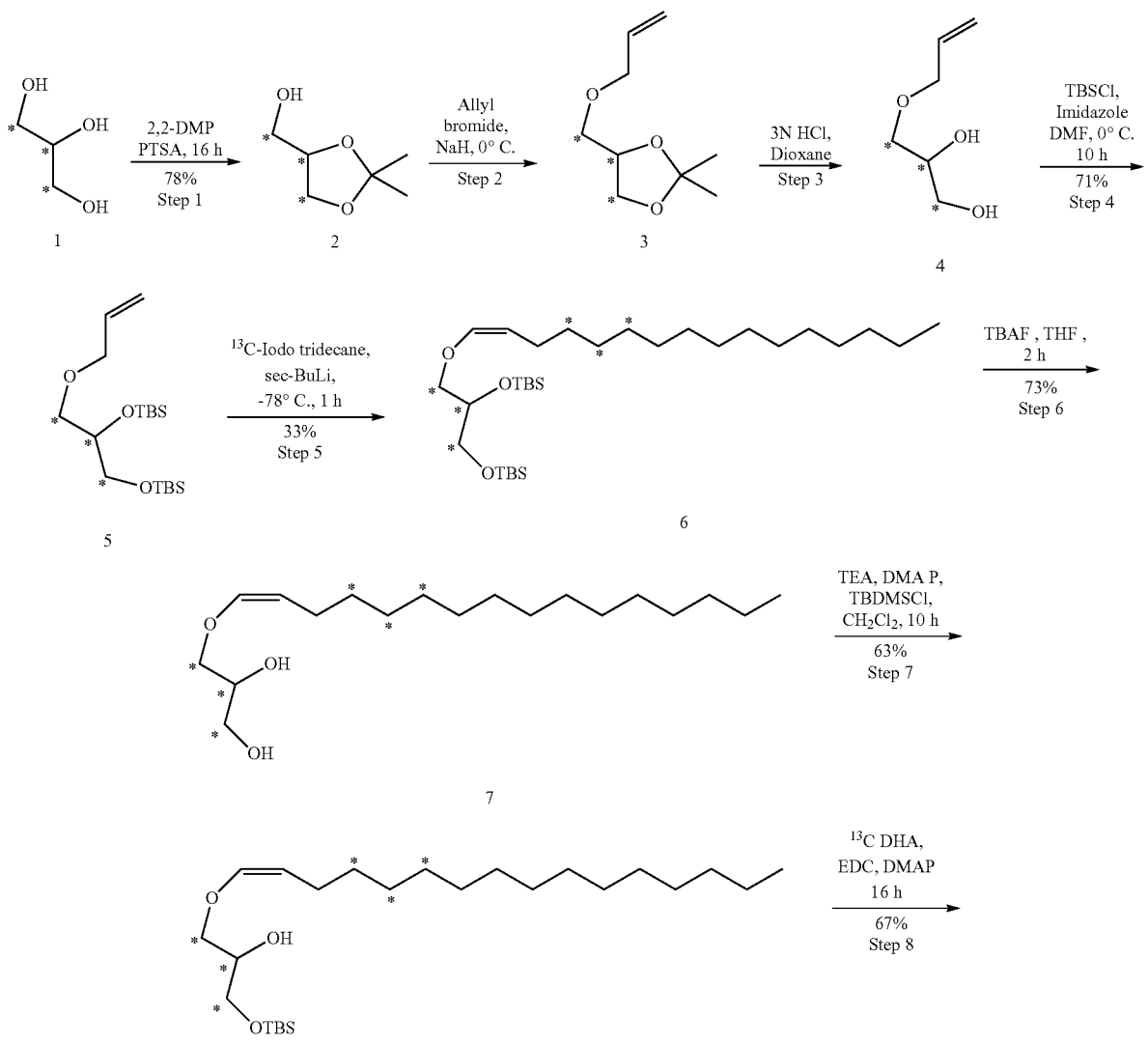

-continued
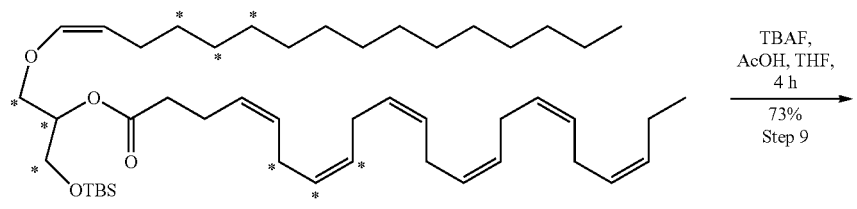
9
TBAF, AcOH, THF, 4 h
73%
Step 9
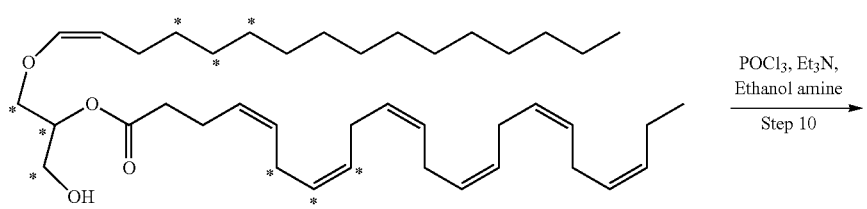
10
POCl$_3$, Et$_3$N, Ethanol amine
Step 10
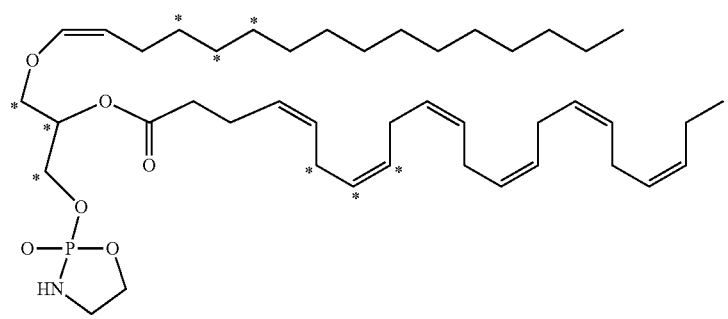
PHE-GLC-10-Cyclic
A non-limiting example of a process for production of the plasmalogen of Formula B in accordance with a preferred embodiment of the invention is depicted in Scheme D:
Scheme D
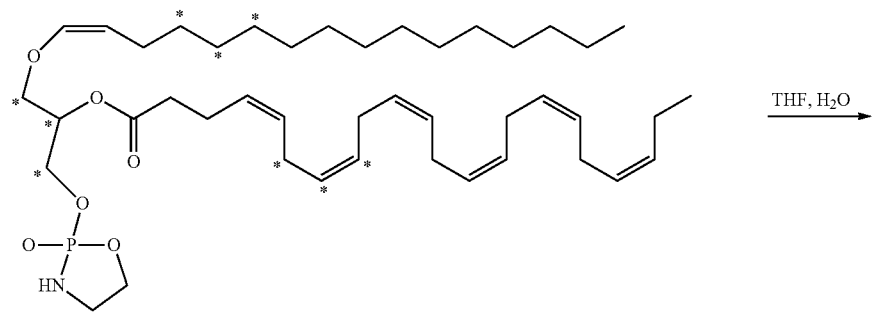
PHE-GLC-10-CYCLIC
THF, H$_2$O

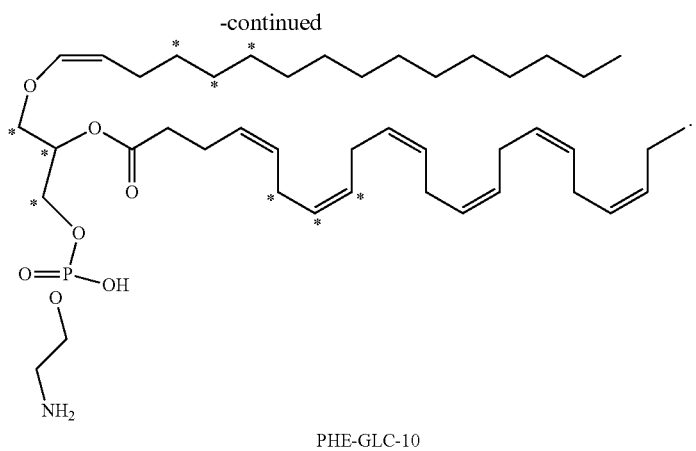

PHE-GLC-10

Example 1

Synthesis of $^{13}$C-Iodotridecane

In a preferred embodiment of the invention, $^{13}$C-iodotridecane is the haloalkane used in the process of synthesizing the plasmalogen precursor. The $^{13}$C-iodotridecane can be obtained by chemical synthesis. The process for the same is explained in details below.

Preparation of Compound Represented by Formula (ii)

In the first step of the synthetic process primary alcohol present propargyl alcohol was protected by ether bond formation, by reacting it with DHA/PTSA resulting in a compound represented by Formula (ii). The reaction scheme involved in this process is as follows:

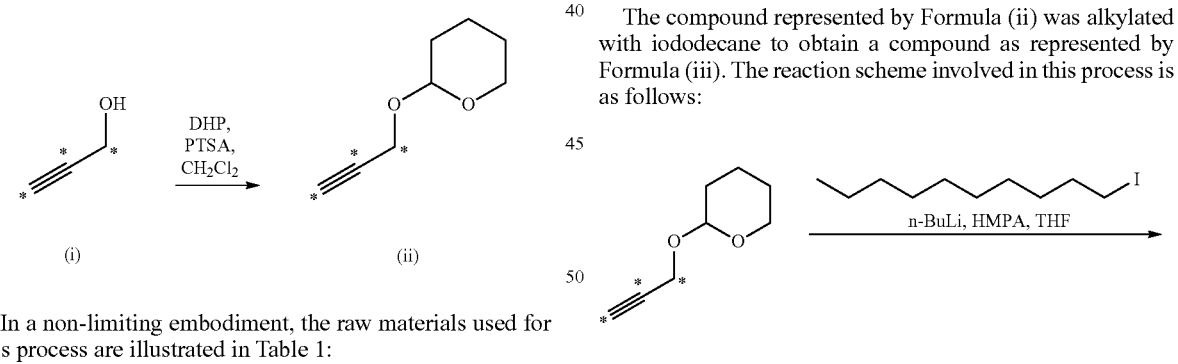

In a non-limiting embodiment, the raw materials used for this process are illustrated in Table 1:

TABLE 1

| S. No. | Name of the Material | Qty. | M. Wt. | mmol | Mole Ratio |
|---|---|---|---|---|---|
| 1. | $^{13}$C labeled propargyl alcohol | 1 g | 56.06 | 16.93 | 1 |
| 2. | Dichloromethane | 15 mL | 84.93 | — | 15 vol. |
| 3. | PTSA | 3 mg | — | 0.16 | 0.009 |
| 4. | DHP | 3 mL | 84.12 | 33.86 | 2 |
| 5. | NaHCO$_3$ | — | 84.01 | — | — |
| 6. | Dichloromethane | 2 x 100 mL | 84.93 | — | 2 x 100 vol. |
| 7. | Water | 2 x 100 mL | 18 | — | 2 x 100 vol. |
| 8. | Brine | 1 x 100 mL | — | — | 100 vol. |

To a solution of propargyl alcohol (represented by Formula (i)) (1 g, 16.93 mmol) in dichloromethane (15 mL), PTSA (3 mg, 0.16 mmol) and DHP (3 mL, 33.86 mmol) were added and the reaction mixture was stirred at room temperature for 2 h. After completion of starting materials, the reaction mixture was quenched with NaHCO$_3$ and extracted with dichloromethane (100 mL×2), washed with water (100 mL×2), and brine (100 mL×1). The combined organic extracts were evaporated under reduced pressure to obtain the crude product which was purified by column chromatography (100-200 mesh silica gel, eluent 10% EtOAc in hexane) to furnish a compound as represented by Formula (ii) (2.078 g, 87%) as a light brown liquid.

Preparation of Compound Represented by Formula (iii)

The compound represented by Formula (ii) was alkylated with iododecane to obtain a compound as represented by Formula (iii). The reaction scheme involved in this process is as follows:

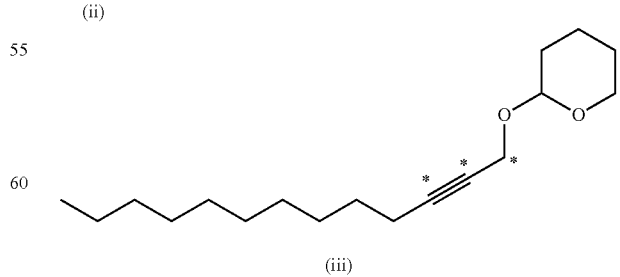

In a non-limiting embodiment, the raw materials used for this process are illustrated in Table 2:

TABLE 2

| S. No. | Name of the Material | Qty. | M. Wt. | mmol | Mole Ratio |
|---|---|---|---|---|---|
| 1. | Compound of Formula (ii) | 2.07 g | 142.76 | 14.5 | 1 |
|  | Iododecane | 3.8 mL | 268.18 | 17.4 | 1.2 |
| 2. | THF | 40 mL | 72.11 | — | 19.32 vol. |
| 3. | HMPA | 3.78 mL | 179.2 | 21.7 | 1.49 |
| 4. | n-BuLi | 7.54 mL | 64.06 | 18.86 | 1.3 |
| 5. | Ethyl acetate | 3 x 30 mL | 88.11 | — | 3 x 14.49 vol. |
| 7. | Water | 25 mL | 18 | — | 12.08 vol. |
| 8. | Brine | 25 mL | — | — | 12.08 vol. |
| 9. | Na$_2$SO$_4$, anhydrous | As needed | 142.04 | — | — |

To a solution of the compound represented by Formula (ii) (2.07 g, 14.5 mmol) in THF (40 mL), HMPA (3.78 mL, 21.7 mmol) and n-BuLi (2.5 M, 7.54 mL, 18.86 mmol) were added drop wise at −78° C. After 1 hour, iododecane (3.8 mL, 17.4 mmol) in THF was added drop wise at −78° C. and stirred at room temperature for 16 h. After completion of starting materials, the reaction mixture was quenched with ice and extracted with ethyl acetate (30 mL×3), washed with water (25 mL×1), brine (25 mL×1) and dried over anhy. Na$_2$SO$_4$. The combined organic extracts were evaporated under reduced pressure to obtain the crude product which was purified by column chromatography (100-200 mesh silica gel, eluent 10% dichloromethane in hexane) to furnish the compound represented by Formula (iii) (1.94 g, 47%) as light yellow liquid.

Preparation of a Compound Represented by Formula (iv)

Hydrogenation of the compound represented by Formula (iii) resulted in a compound represented by Formula (iv). The reaction scheme involved in this process is as follows:

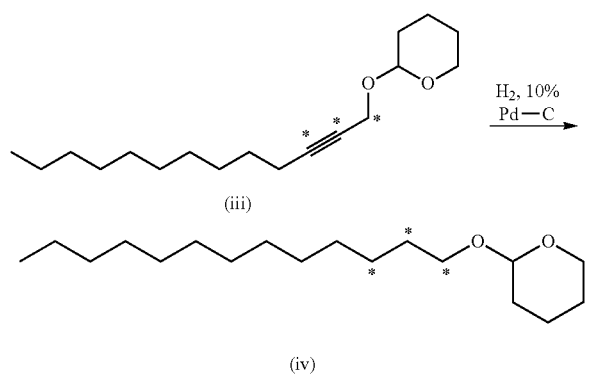

In an exemplary embodiment, the raw materials used for this process are illustrated in Table 3:

TABLE 3

| S. No. | Name of the Material | Qty. | M. Wt. | mmol | Mole Ratio |
|---|---|---|---|---|---|
| 1. | Compound of Formula (iii) | 870 mg | 284.31 | 3.06 | 1 |
| 2. | Pd/C (10%) | 100 mg | — | — | — |
| 3. | Ethyl acetate | 2 x 30 mL | 88.11 | — | 2 x 9.8 vol. |

To a solution of the compound represented by Formula (iii) (870 mg, 3.06 mmol) in ethyl acetate (10 mL), 10% Pd/C (100 mg) was added and the reaction was stirred under hydrogen atmosphere for 12 h. After completion of starting material, the reaction mass was filtered through a Celite™ pad and washed with ethyl acetate (30 mL×2) twice. The combined organic extracts were evaporated under reduced pressure to obtain the crude product which was purified by column chromatography (100-200 mesh silica gel, 5% ethyl acetate in hexane) to furnish the compound represented by Formula (iv) (800 mg, 90%) as colorless liquid.

Preparation of a Compound Represented by Formula (v)

THP present in the compound of Formula (iv) was deprotected to produce the compound represented by Formula (v). The reaction scheme involved in this process is as follows:

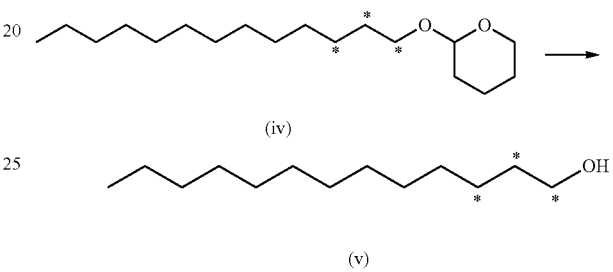

In an exemplary embodiment, the raw materials used for this process are illustrated in Table 4:

TABLE 4

| S. No. | Name of the Material | Qty. | M. Wt. | mmol | Mole Ratio |
|---|---|---|---|---|---|
| 1. | Compound of Formula (iv) | 1.1 g | 287.96 | 3.82 | 1 |
| 2. | Methanol | 10 mL | 32 | — | 9.09 vol. |
| 3. | PTSA | 65 mg | — | 0.37 | 0.097 |
| 4. | NaHCO$_3$ | — | 84.01 | — | — |
| 5. | Ethyl acetate | 2 x 50 mL | 88.11 | — | 2 x 45.45 vol. |
| 6. | Water | 100 mL | — | — | 90.90 vol. |
| 7. | Brine | 50 mL | — | — | 45.45 vol. |
| 8. | Na$_2$SO$_4$ | As needed | 142.04 | — | — |

To a solution of compound represented by Formula 4 (1.1 g, 3.82 mmol) in methanol (10 mL), PTSA (65 mg, 0.37 mmol) was added and the reaction was stirred at room temperature for 2 h. After completion of starting material, the reaction mixture was quenched with NaHCO$_3$ and concentrated, extracted with ethyl acetate (50 mL×2) washed with water (100 mL×1), brine (50 mL×1) and dried over Na$_2$SO$_4$. The combined organic extracts were evaporated under reduced pressure to obtain the crude product which was purified by column chromatography (100-200 mesh silica gel, 30% dichloromethane in hexane) to furnish the compound represented by Formula (v) (700 mg, 90%) as a colorless liquid.

Preparation of Iodotridecane

The compound of Formula (v) was converted to iodotridecane by iodination of the primary alcohol present in the compound of Formula (v). The reaction scheme involved in this process is as follows:

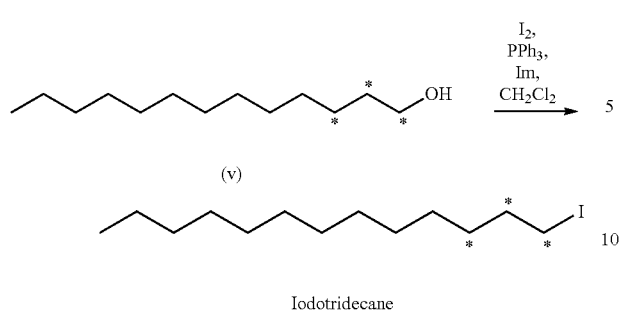

Iodotridecane

In an exemplary embodiment, the raw materials used for this process are illustrated in Table 5:

TABLE 5

| S. No. | Name of the Material | Qty. | M. Wt. | mmol | Mole Ratio |
|---|---|---|---|---|---|
| 1. | Compound of Formula (v) | 1.08 g | 203.39 | 5.31 | 1 |
| 2. | $I_2$ | 1.48 g | 253 | 5.84 | 1.1 |
| 3. | Dichloromethane | 20 mL | 84.93 | — | 18.52 vol. |
| 4. | Triphenyl phosphine | 1.53 g | 262.29 | 5.84 | 1.1 |
| 5. | Imidazole | 0.39 g | 68.07 | 5.84 | 1.1 |

To a solution of tridecanol (1.08 g, 5.31 mmol) in dichloromethane (20 mL), triphenyl phosphine (1.53 g, 5.84 mmol) and imidazole (0.39 g, 5.84 mmol) were added and cooled to 0° C. $I_2$ (1.48 g, 5.84 mmol) was added and the reaction mixture was stirred at room temperature for 3 h. After completion of starting materials, the reaction mixture was evaporated and diluted with hexane and passed through a Celite™ pad. The combined organic extracts were evaporated under reduced pressure to obtain the crude product which was purified by column chromatography (100-200 mesh silica gel, eluent hexane) to furnish iodotridecane (1.43 g, 84%) as a low melting solid.

Example 2

Synthesis of $^{13}$C-DHA

In a preferred embodiment of the invention, $^{13}$C-DHA is the fatty acid used in the process of synthesizing the plasmalogen precursor. The $^{13}$C-DHA can be obtained by chemical synthesis, and an example of this process is explained in detail below.

Preparation of a Compound of Formula 2(ii)
(Pent-2-ynyl 4-methylbenzenesulfonate)

In the first step of the synthetic process, 2-pentyn-1-ol of Formula 2(i) is converted to the tosyl compound represented by Formula 2(ii) using tosyl chloride in the presence of KOH. The reaction scheme involved in this process is as follows:

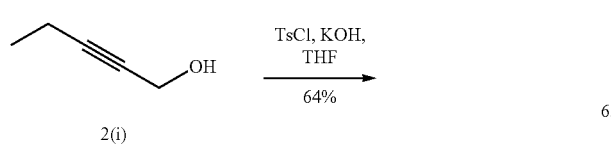

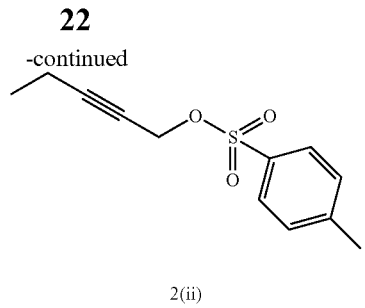

In an exemplary embodiment, the raw materials used for this step are illustrated in Table 1:

TABLE 1

| S. No. | Name of the Material | Qty. | M. Wt. | Moles | Mole Ratio |
|---|---|---|---|---|---|
| 1. | 2-Pentyn-1-ol | 60 g | 84.12 | 0.71 | 1 |
| 2. | Tosyl Chloride (TsCl) | 142.9 g | 190.65 | 0.75 | 1.06 |
| 3. | KOH | 79.9 g | 56.11 | 1.42 | 2 |
| 4. | THF | 420 mL | 72.11 | — | 7 vol. |
| 5. | Ethyl Acetate | 600 mL | 88.11 | — | 10 vol. |
| 6. | Water | 2 x 100 mL | 18 | — | 2 x 1.67 vol. |
| 7. | Brine | 2 x 50 mL | — | — | 2 x 0.83 vol. |
| 8. | $Na_2SO_4$ | As needed | 142.04 | — | — |

To a solution of 2-Pentyn-1-ol (60 g, 0.71 mol) in THF (420 mL) cooled to −5° C., tosyl chloride (142.9 g, 0.75 mol) and KOH (79.9 g, 1.42 mol) were added and the reaction mixture was stirred at room temperature for 1 h. After completion of starting material, the reaction mixture was extracted with ethyl acetate (300 mL×2), washed with water (100 mL×2), brine (50 mL×2) and dried over $Na_2SO_4$. The combined organic extracts were evaporated under reduced pressure to obtain the crude product which was purified by column chromatography (100-200 mesh silica gel, 20% EtOAc-hexane) to furnish pent-2-ynyl 4-methylbenzenesulfonate (110 g, 64%) as a light red liquid.

Preparation of a Compound of Formula 2(iii)
(Octa-2,5-diyn-1-ol)

The Compound of Formula 2(ii) obtained above, was coupled with propargyl alcohol in the presence of CuI, $K_2CO_3$ and TBAI to produce the compound represented by Formula 2(iii). The reaction scheme involved in this process is as follows:

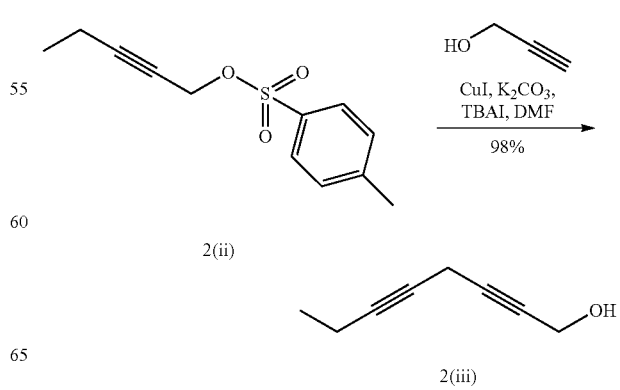

In an exemplary embodiment, the raw materials used for this step are illustrated in Table 2:

TABLE 2

| S. No. | Name of the Material | Qty. | M. Wt. | Moles | Mole Ratio |
|---|---|---|---|---|---|
| 1. | Compound of Formula 2(ii) | 60 g | 84.5 | 0.71 | 1 |
| 2. | Propargyl alcohol | 15.52 g | 56.06 | 0.27 | 0.38 |
| 3. | Potassium Carbonate | 47.8 g | 138.2 | 0.34 | 0.48 |
| 4. | CuI | 43.9 g | 190.45 | 0.23 | 0.32 |
| 5. | TBAI | 85.30 g | 369.37 | 0.23 | 0.32 |
| 6. | DMF | 440 mL | 73.09 | — | 7.33 vol. |
| 7. | Ethyl acetate | 2 x 300 mL | 88.11 | — | 2 x 5 vol. |
| 8. | Cold water | 2 x 200 mL | 18 | — | 2 x 3.33 vol. |
| 9. | Brine | 2 x 100 mL | — | — | 2 x 1.67 vol. |
| 10. | $Na_2SO_4$, anhydrous | As needed | 142.04 | — | — |

To a stirred solution of potassium carbonate (47.8 g, 0.34 mol), CuI (43.9 g, 0.23 mol), and TBAI (85.30 g, 0.23 mol) in DMF (440 mL) cooled to 0° C., propargyl alcohol (15.52 g, 0.27 mol) was added portion wise at room temperature followed by the compound represented by Formula 2(ii) (55 g, 0.23 mol) and the reaction mixture was stirred at room temperature for 16 h. After completion of starting materials, the reaction mixture was cooled to 0° C. and diluted with cold water, ethyl acetate (300 mL×2), filtered through a Celite™ bed and washed with ethyl acetate. The combined organic extracts were washed with cold water (200 mL×2), brine (100 mL×2) and dried over anhydrous $Na_2SO_4$. Solvent was evaporated under reduced pressure to obtain the crude product which was purified by column chromatography (100-200 mesh silica gel, 20% EtOAc in hexane) to furnish octa-2,5-diyn-1-ol (55 g, 98%) as a light red liquid.

Preparation of Compound of Formula 2(iv)
(1-bromoocta-2,5-diyne)

The compound of Formula 2(iii) was then brominated with $PBr_3$ to produce the compound represented by Formula 2(iv). The reaction scheme involved in this process is as follows:

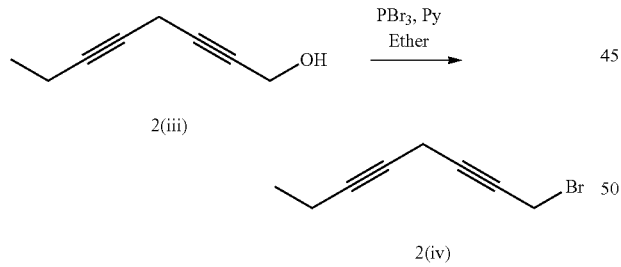

In an exemplary embodiment, the raw materials used for this step are illustrated in Table 3:

TABLE 3

| S. No. | Name of the Material | Qty. | M. Wt. | Moles | Mole Ratio |
|---|---|---|---|---|---|
| 1. | Compound of Formula 2(iii) | 55 g | 122.22 | 0.45 | 1 |
| 2. | $PBr_3$ | 17.13 mL | 270.69 | 0.18 | 0.4 |
| 3. | Diethylether | 550 mL | 74.12 | — | 10 vol. |
| 4. | Pyridine | 3.6 mL | 79.1 | 0.04 | 0.009 |
| 5. | Ethyl acetate | 2 x 200 mL | 88.11 | — | 2 x 3.63 vol. |
| 6. | Cold water | 100 mL | 18 | — | 1.82 vol. |

TABLE 3-continued

| S. No. | Name of the Material | Qty. | M. Wt. | Moles | Mole Ratio |
|---|---|---|---|---|---|
| 7. | Brine | 100 mL | — | — | 1.82 vol. |
| 8. | $Na_2SO_4$, anhydrous | As needed | 142.04 | — | — |

To a stirred solution of compound 2(iii) (55 g, 0.45 mol) in diethylether (550 mL) cooled to 0° C., pyridine (3.6 mL, 0.04 mol) and $PBr_3$ (17.13 mL, 0.18 mol) were added at 0° C. and the reaction mixture was stirred at room temperature for 16 h. After the completion of starting material, the reaction mixture was cooled to 0° C., diluted with cold water, and extracted with ethyl acetate (200 mL×2). The combined organic extracts were washed with cold water (100 mL×1), brine (100 mL×1), dried over anhydrous $Na_2SO_4$ and evaporated under reduced pressure to furnish 1-bromoocta-2,5-diyne (75 g, crude) as a red liquid which was carried to the next step without further purification.

Preparation of a Compound of Formula 2(v)
(undeca-2,5,8-triyn-1-ol)

The compound of Formula 2(iv) obtained above was coupled with propargyl alcohol to produce the compound of Formula 2(v). The reaction scheme involved in this process is as follows:

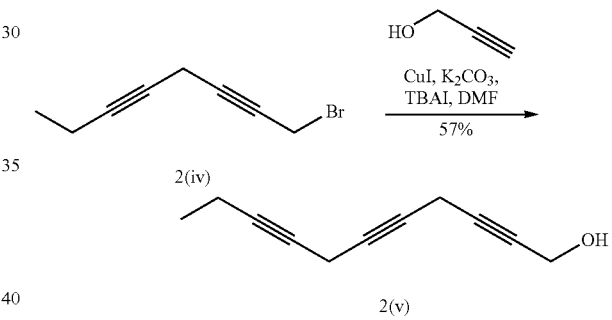

In an exemplary embodiment, the raw materials used for this step are illustrated in Table 4:

TABLE 4

| S. No. | Name of the Material | Qty. | M. Wt. | Moles | Mole Ratio |
|---|---|---|---|---|---|
| 1. | Compound of Formula 2(iv) | 75 g | 187.5 | 0.40 | 1 |
| 2. | Propargyl alcohol | 27.2 g | 56.06 | 0.48 | 1.2 |
| 3. | Potassium Carbonate | 83 g | 138.2 | 0.60 | 1.5 |
| 4. | CuI | 77 g | 190.45 | 0.40 | 1 |
| 5. | TBAI | 149.5 g | 369.37 | 0.40 | 1 |
| 6. | DMF | 450 mL | 73.09 | — | 6 vol. |
| 7. | Ethyl acetate | 300 mL | 88.11 | — | 4 vol. |
| 8. | Cold water | 2 x 100 mL | 18 | — | 2 x 1.33 vol. |
| 9. | Brine | 100 mL | — | — | 1.33 vol. |
| 10. | $Na_2SO_4$ | As needed | 142.04 | — | — |

To a stirred solution of potassium carbonate (83 g, 0.60 mol), CuI (77 g, 0.40 mol) and TBAI (149.5 g, 0.40 mol) in DMF (450 mL) cooled to 0° C., propargyl alcohol (27.2 g, 0.48 mol) and the compound represented by Formula 2(iv) (75 g, 0.40 mol) were sequentially added and stirred at room temperature for 16 h. After the completion of starting materials, the reaction mixture was cooled to 0° C. and diluted with cold water, ethyl acetate (300 mL), filtered through a Celite™ pad using a Buchner funnel and washed with ethyl acetate. The filtrate was taken and the organic layers were separated. The combined organic extracts were washed with cold water (100 mL×2), brine solution (100 mL×1), dried over Na₂SO₄ and evaporated under reduced pressure to obtain the crude product which was purified by column chromatography (100-200 mesh silica gel, 20% EtOAc in hexane) to furnish undeca-2,5,8-triyn-1-ol (37 g, 57%) as a pale yellow liquid.

Preparation of a Compound of Formula 2(vi)
(1-bromoundeca-2,5,8-triyne)

The compound of Formula 2(v) was then brominated with PBr₃ to produce the compound of Formula 2(vi). The reaction scheme involved in this process is as follows:

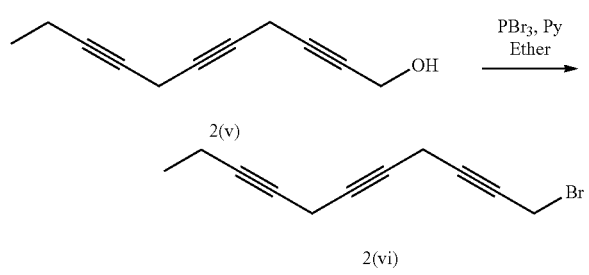

In an exemplary embodiment, the raw materials used for this step are illustrated in Table 5:

TABLE 5

| S. No. | Name of the Material | Qty. | M. Wt. | Moles | Mole Ratio |
|---|---|---|---|---|---|
| 1. | Compound of Formula 2(v) | 37 g | 160.87 | 0.23 | 1 |
| 2. | PBr₃ | 0.79 mL | 270.69 | 0.09 | 0.39 |
| 3. | Diethylether | 370 mL | 74.12 | — | — |
| 4. | Pyridine | 1.86 mL | 79.1 | 0.02 | 0.09 |
| 5. | Ethyl acetate | 100 mL | 88.11 | — | 2.7 vol. |
| 6. | Cold Water | 2 × 50 mL | 18 | — | 2 × 1.35 vol. |
| 7. | Brine | 50 mL | — | — | 1.35 vol. |
| 8. | Na₂SO₄ | As needed | 142.04 | — | — |

To a stirred solution of the compound represented by Formula 2(v) (37 g, 0.23 mol) in ether (370 mL) cooled to 0° C., pyridine (1.86 mL, 0.02 mol) and PBr₃ (0.79 mL, 0.09 mol) were added at 0° C. and stirred at room temperature for 16 h. After the completion of starting material, the reaction mixture was cooled to 0° C. and diluted with cold water, extracted with ethyl acetate (100 mL). The combined organic extracts were washed with cold water (50 mL×2), brine solution (50×1), dried over Na₂SO₄ and evaporated under reduced pressure to furnish 1-bromoundeca-2,5,8-triyne (42 g, crude) as a pale yellow color liquid which was carried to the next step without further purification.

Preparation of Compound of Formula 2(vii)
(tetradeca-2,5,8,11-tetrayn-1-ol)

The Bromide of Formula 2(vi) was coupled with propargyl alcohol to produce the compound of Formula 2(vii). The reaction scheme involved in this process is as follows:

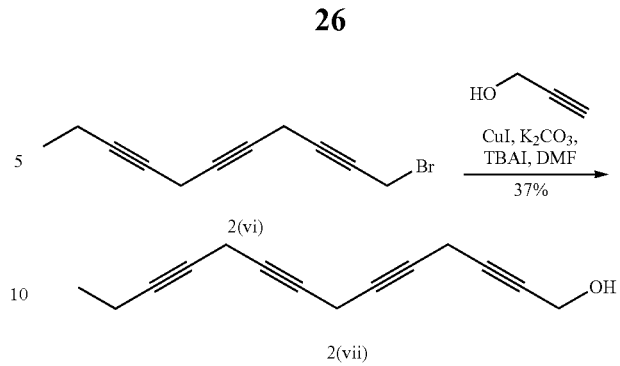

In an exemplary embodiment, the raw materials used for this step are illustrated in Table 6:

TABLE 6

| S. No. | Name of the Material | Qty. | M. Wt. | Moles | Mole Ratio |
|---|---|---|---|---|---|
| 1. | Compound of Formula 2(vi) | 42 g | 233.33 | 0.18 | 1 |
| 2. | Propargyl alcohol | 14 g | 56.06 | 0.25 | 1.39 |
| 3. | Potassium Carbonate | 38 g | 138.2 | 0.27 | 1.5 |
| 4. | CuI | 35.85 g | 190.45 | 0.18 | 1 |
| 5. | TBAI | 69.5 g | 369.37 | 0.18 | 1 |
| 6. | DMF | 250 mL | 73.09 | — | 5.95 vol. |
| 7. | Cold water | 200 mL | 18 | — | 4.76 vol. |
| 8. | Ethyl acetate | 200 mL | 88.11 | — | 4.76 vol. |
| 9. | Ethyl acetate | 2 × 100 mL | 88.11 | — | 2 × 2.38 vol. |
| 10. | Cold Water | 2 × 50 mL | 18 | — | 2 × 1.19 vol. |
| 12. | Brine | 50 mL | — | — | 1.19 vol. |
| 11. | Na₂SO₄ | As needed | 142.04 | — | — |

To a solution of potassium carbonate (38 g, 0.27 mol), CuI (35.85 g, 0.18 mol) and TBAI (69.5 g, 0.18 mol) in DMF (250 mL) cooled to 0° C., propargyl alcohol (14 g, 0.25 mol) and the compound represented by Formula 2(vi) (42 g, 0.18 mol) were added drop wise for 30 min and stirred for 16 h at room temperature. After the completion of starting material, the reaction mixture was cooled to 0° C. and diluted with cold water (200 mL), ethyl acetate (200 mL), filtered through a Celite™ bed using Buchner funnel and washed with ethyl acetate (100 mL×2). The organic layer were separated and the combined organic extracts were washed with cold water (50 mL×2), brine solution (50 mL×1), dried over Na₂SO₄ and evaporated under reduced pressure to obtain the crude product which was purified by column chromatography (100-200 mesh silica gel, 20% EtOAc in hexane) to furnish tetradeca-2,5,8,11-tetrayn-1-ol (12 g, 32%) as a pale yellow solid.

Preparation of a Compound of Formula 2(viii)
(1-bromotetradeca-2,5,8,11-tetrayne)

The Compound of Formula 2(vii) was brominated with PBr₃ to produce the compound of Formula 2(viii). The reaction scheme involved in this process is as follows:

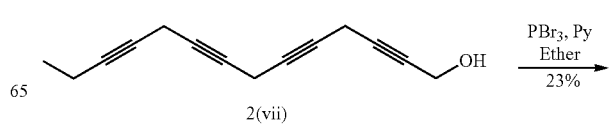

-continued

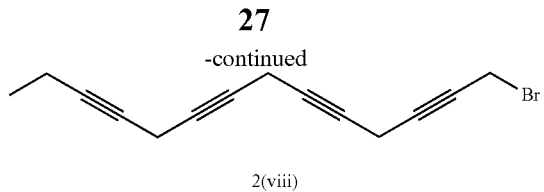

2(viii)

In an exemplary embodiment, the raw materials used for this step are illustrated in Table 7:

TABLE 7

| S. No. | Name of the Material | Qty. | M. Wt. | mM | Mole Ratio |
|---|---|---|---|---|---|
| 1. | Compound of Formula 2(vii) | 7.5 g | 198.4 | 37.8 | 1 |
| 2. | PBr₃ | 1.44 mL | 270.69 | 15.15 | 0.4 |
| 3. | Dichloromethane | 75 mL | 84.93 | — | 10 vol. |
| 4. | Pyridine | 0.3 mL | 79.1 | 3.78 | 0.1 |
| 5. | Dichloromethane | 2 x 100 mL | 84.93 | — | 2 x 13.33 vol. |
| 6. | Water | 2 x 25 mL | 18 | — | 2 x 3.33 vol. |
| 7. | Brine | 2 x 25 mL | — | — | 2 x 3.33 vol. |
| 8. | Na₂SO₄ | As needed | 142.04 | — | — |

To a stirred solution of the compound represented by Formula 2(vii) (7.5 g, 37.8 mmol) in dry dichloromethane (75 mL), cooled to 0° C., pyridine (0.3 mL, 3.78 mmol) and PBr₃ (1.44 mL, 15.15 mmol) were added at 0° C., then the reaction mixture was stirred at room temperature for 16 h. After the completion of starting material, the reaction mixture was quenched with ice cold water and then extracted with dichloromethane (100 mL×2). The combined organic extracts were washed with water (25 mL×2), brine (25 mL×2), dried over Na₂SO₄ and evaporated under reduced pressure to obtain the crude product which was purified by column chromatography (100-200 mesh silica gel, 1% EtOAc in hexane) to furnish 1-bromotetradeca-2,5,8,11-tetrayne (2.3 g, 23%) as a yellow color solid.

Preparation of a Compound of Formula 2(ix) (heptadeca-2,5,8,11,14-pentayn-1-ol)

The compound of Formula 2(viii) was coupled with ¹³C labeled propargyl alcohol to produce the compound of Formula 2(ix). The reaction scheme involved in this process is as follows:

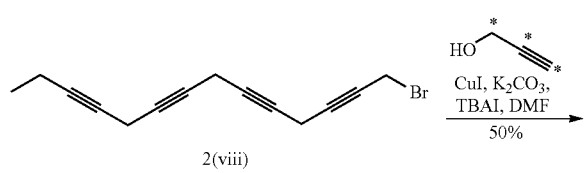

-continued

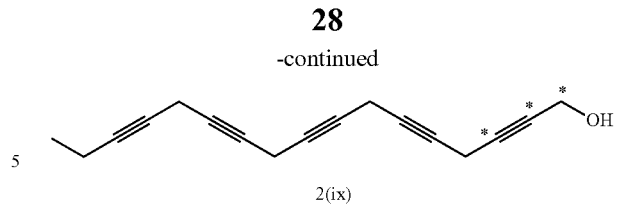

2(ix)

In an exemplary embodiment, the raw materials used for this step are illustrated in Table 8:

TABLE 8

| S. No. | Name of the Material | Qty. | M. Wt. | mM | Mole Ratio |
|---|---|---|---|---|---|
| 1. | Compound of Formula 2(viii) | 1.7 g | 280.34 | 6.53 | 1 |
| 2. | ¹³C labeled Propargyl alcohol | 0.36 g | 56.06 | 6.42 | 0.98 |
| 3. | Potassium Carbonate | 1.35 g | 138.2 | 9.78 | 1.49 |
| 4. | CuI | 1.24 g | 190.45 | 6.53 | 1 |
| 5. | TBAI | 2.41 g | 369.37 | 6.53 | 1 |
| 6. | DMF | 14 mL | 73.09 | — | 8.23 vol. |
| 7. | Cold water | 10 mL | 18 | — | 5.88 vol. |
| 8. | Ethyl acetate | 2 x 50 mL | 88.11 | — | 2 x 29.41 vol. |
| 9. | Cold Water | 2 x 25 mL | 18 | — | 2 x 14.7 vol. |
| 10. | Brine | 25 mL | — | — | 14.7 vol. |
| 11. | Na₂SO₄ | As needed | 142.04 | — | — |

To a stirred solution of potassium carbonate (1.35 g, 9.78 mmol), CuI (1.24 g, 6.53 mmol) and TBAI (2.41 g, 6.53 mmol) in DMF (14 mL) cooled to 0° C., ¹³C labeled propargyl alcohol (0.36 g, 6.42 mmol) and the compound represented by Formula 2(viii) (1.7 g, 6.53 mmol) were added drop wise and stirred at room temperature for 16 h. After completion of starting materials, the reaction mixture was cooled to 0° C. and diluted with cold water (10 mL), ethyl acetate (50 mL×2), filtered through a Celite™ pad using a Buchner funnel and washed with ethyl acetate. The filtrate was taken and the organic layer was separated using a separating funnel. The combined organic extracts were washed with cold water (25 mL×2), brine solution (25 mL×1), dried over Na₂SO₄ and evaporated under reduced pressure to obtain the crude product which was purified by column chromatography (100-200 mesh silica gel, 16% EtOAc in hexane) to furnish heptadeca-2,5,8,11,14-pentayn-1-ol (750 mg, 50%) as a yellow solid.

Preparation of a Compound of Formula 2(x)

The ¹³C labeled compound for Formula 2(ix) obtained above was selectively reduced with Lindlar's Catalyst to produce the compound represented by Formula 2(x). The reaction scheme involved in this process is as follows:

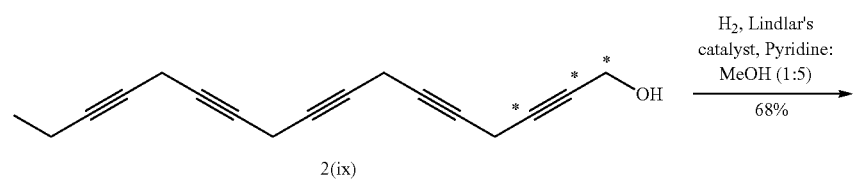

2(ix)

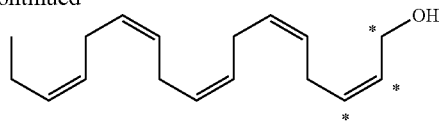

2(x)

In an exemplary embodiment, the raw materials used for this step are illustrated in Table 9:

TABLE 9

| S. No. | Name of the Material | Qty. | M. Wt. | mM | Mole Ratio |
|---|---|---|---|---|---|
| 1. | Compound of Formula 2(ix) | 1.4 g | 239.31 | 5.85 | 1 |
| 2. | Lindlar's catalyst | 1.44 g | — | — | — |
| 3. | Methanol/Pyridine (5:1) | 24 mL | — | — | 17.14 vol. |
| 4. | Methanol | — | 32 | — | — |
| 5. | Ethyl acetate | 2 x 50 mL | 88.11 | — | 2 x 35.71 vol. |
| 6. | 1N HCl | 10 mL | 36.5 | — | 7.14 vol. |
| 7. | Brine | 10 mL | — | — | 7.14 vol. |
| 8. | $Na_2SO_4$ | As needed | 142.04 | — | — |

To a stirred solution of the compound represented by Formula 2(ix) (1.4 g, 5.85 mmol) in methanol/pyridine (5:1, 24 mL), Lindlar's catalyst (1.4 g, w/w) was added. The reaction mixture was stirred under $H_2$ atmosphere at room temperature for 16 h. After completion of starting material, the reaction mixture was filtered through a Celite™ pad and washed with methanol. The solvent was evaporated under reduced pressure and the crude obtained was extracted with ethyl acetate (50 mL×2), and washed with 1N HCl solution (10 mL×1), brine solution (10 mL×1) and dried over $Na_2SO_4$. The combined organic extracts were evaporated under reduced pressure to obtain the crude product which was purified by column chromatography (100-200 mesh silica gel, 10% EtOAc in hexane) to furnish the compound represented by Formula 2(x) (1.0 g, 68%) as a colorless liquid.

Preparation of a Compound of Formula 2(xi)

The compound of Formula 2(x) obtained above was brominated with $PBr_3$ to produce the compound of Formula 2(xi). The reaction scheme involved in this process is as follows:

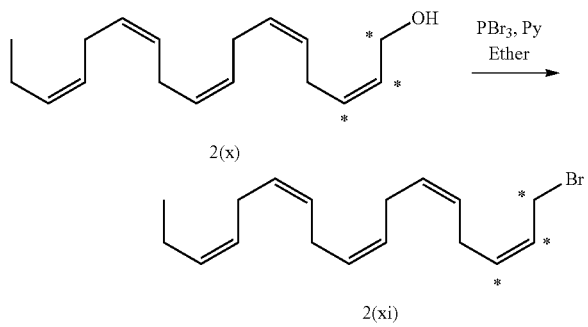

TABLE 10

| S. No. | Name of the Material | Qty. | M. Wt. | mM | Mole Ratio |
|---|---|---|---|---|---|
| 1. | Compound of Formula 2(x) | 1.2 g | 249.28 | 4.81 | 1 |
| 2. | $PBr_3$ | 0.52 g | 270.69 | 1.92 | 0.4 |
| 3. | Dichloromethane | 20 mL | 84.93 | — | 16.67 vol. |
| 4. | Pyridine | 0.38 mL | 79.1 | 0.48 | 0.1 |
| 5. | Cold water | 10 mL | 18 | — | 8.33 vol. |
| 6. | Dichloromethane | 2 × 50 mL | 84.93 | — | 41.67 vol. |
| 7. | Water | 15 mL | 18 | — | 12.5 vol. |
| 8. | Brine | 20 mL | — | — | 16.67 vol. |
| 9. | $Na_2SO_4$ | As needed | 142.04 | — | — |

To a solution of compound represented by Formula 2(x) (1.2 g, 4.81 mmol) in dry dichloromethane (20 mL) and pyridine (0.038 mL, 0.48 mmol) cooled to 0° C., $PBr_3$ (0.52 g, 1.92 mmol) was added drop wise and stirred at room temperature for 2 h. After completion of starting material, the reaction mixture was quenched with ice cold water (10 mL×1) and extracted with dichloromethane (50 mL×2). The combined organic extracts were washed with water (15 mL×1), brine (20 mL×1), dried over $Na_2SO_4$ and evaporated under reduced pressure to furnish the compound represented by Formula 2(xi) (1.2 g, crude) as a yellow liquid which was carried to the next step without further purification.

Preparation of Compound of Formula 2(xii)

The compound of Formula 2(xi) was coupled with methylpent-4-yonate to produce the compound represented by Formula 2(xii). The reaction scheme involved in this process is as follows:

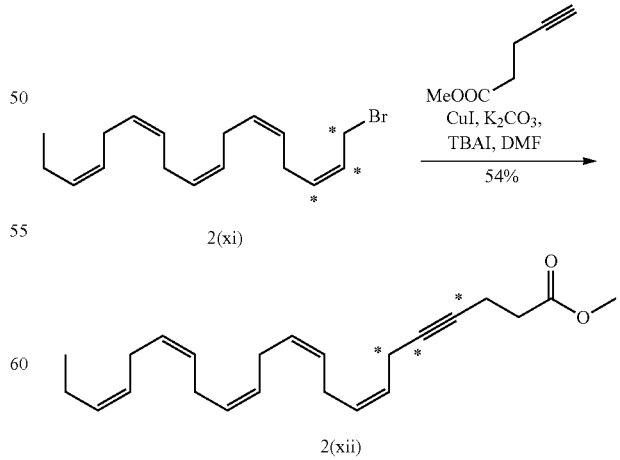

In an exemplary embodiment, the raw materials used for this step are illustrated in Table 10:

In an exemplary embodiment, the raw materials used for this step are illustrated in Table 11:

TABLE 11

| S. No. | Name of the Material | Qty. | M. Wt. | mM | Mole Ratio |
|---|---|---|---|---|---|
| 1. | Compound of Formula 2(xi) | 200 mg | 312.5 | 0.64 | 1 |
| 2. | Methyl-pent-4-yonate | 86 mg | 111 | 0.76 | 1.19 |
| 3. | Potassium Carbonate | 132 mg | 138.2 | 0.96 | 1.5 |
| 4. | CuI | 112 mg | 190.45 | 0.64 | 1 |
| 5. | TBAI | 236 mg | 369.37 | 0.64 | 1 |
| 6. | DMF | 10 mL | 73.09 | — | 50 vol. |
| 7. | Cold Water | 10 mL | 18 | — | 50 vol. |
| 8. | Diethyl ether | 2 × 25 mL | 74.12 | — | 2 × 125 vol. |
| 9. | Water | 10 mL | 18 | — | 50 vol. |
| 10. | Brine | 10 mL | — | — | 50 vol. |
| 11. | $Na_2SO_4$ | As needed | 142.04 | — | — |

To a solution of potassium carbonate (132 mg, 0.96 mmol), CuI (121 mg, 0.64 mmol) and TBAI (236 mg, 0.64 mmol) in dry DMF (10 mL) cooled to 0° C., methyl pent-4-ynoate (86 mg, 0.76 mmol) and the compound represented by Formula 2(xi) (200 mg, 0.64 mmol) in DMF were added and stirred at room temperature for 16 h. After completion of starting material, the reaction mixture was quenched with ice cold water (10 mL) and filtered through a Celite™ bed and washed with diethyl ether (25 mL×2), water (10 mL×1), brine solution (10 mL×1) and dried over $Na_2SO_4$. The combined organic extracts were evaporated under reduced pressure to obtain the crude product which was purified by column chromatography (100-200 mesh silica gel, eluted at 2% EtOAc in hexane) to furnish the compound represented by Formula 2(xii) (120 mg, 54%) as a colorless liquid.

Preparation of a Compound of Formula 2(xiii)

The compound of Formula 2(xii) obtained above was selectively reduced with Lindlar's catalyst to produce the compound of Formula 2(xiii). The reaction scheme involved in this process is as follows:

In an exemplary embodiment, the raw materials used for this step are illustrated in Table 12:

TABLE 12

| S. No. | Name of the Material | Qty. | M. Wt. | mM | Mole Ratio |
|---|---|---|---|---|---|
| 1. | Compound of Formula 2(xii) | 500 mg | 344.82 | 1.45 | 1 |
| 2. | Lindlar's catalyst | 500 mg | — | — | — |
| 3. | Methanol/Pyridine (4:1) | 10 mL | — | — | 20 vol. |
| 4. | Methanol | 20 mL | 32 | — | 40 vol. |
| 5. | Ethyl acetate | 2 × 30 mL | 88.11 | — | 2 × 60 vol. |
| 6. | 1N HCl | 10 mL | 36.5 | — | 20 vol. |
| 7. | Brine | 15 mL | — | — | 30 vol. |
| 8. | $Na_2SO_4$ | As needed | 142.04 | — | — |

To a solution of compound represented by Formula 2(xii) (500 mg, 1.45 mmol) in dry methanol/pyridine(10 mL, 4:1), Lindlar's catalyst (500 mg, w/w) was added. The reaction mixture was stirred under $H_2$ atmosphere at room temperature for 16 h. Additionally, Lindlar's catalyst (250 mg) was added two times at 4 h interval and the reaction mixture was stirred under $H_2$ atmosphere. The reaction mixture was filtered through a Celite™ pad, washed with methanol (20 mL) and evaporated under reduced pressure. The crude obtained was extracted with ethyl acetate (30 mL×2), washed with 1N HCl solution (10 mL×1), brine solution (15 mL×1) and dried over $Na_2SO_4$. The combined organic layer was evaporated under reduced pressure to furnish the compound represented by Formula 2(xiii) (400 mg, 80%) as a pale yellow liquid.

Preparation of $^{13}C$ DHA

In the last step of the 13-step synthetic process, $^{13}C$ DHA was obtained by ester hydrolysis of the compound represented by Formula 2(xiii) in the presence of lithium hydroxide. The reaction scheme involved in this process is as follows:

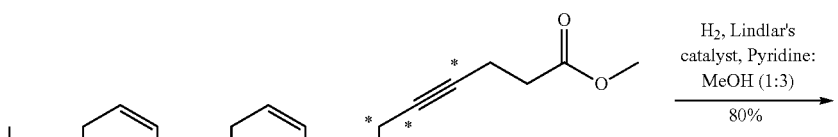

2(xii)

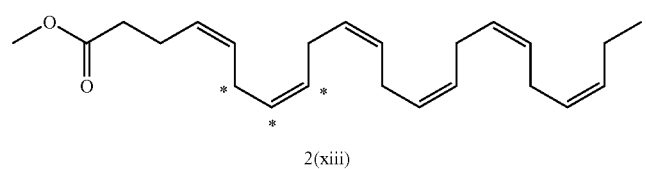

2(xiii)

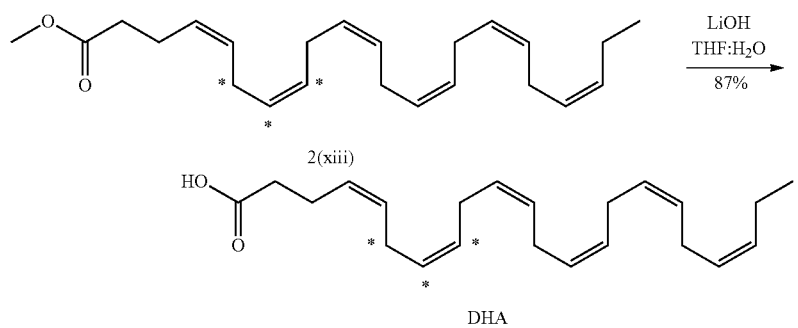

In an exemplary embodiment, the raw materials used for this step are illustrated in Table 13:

TABLE 13

| S. No. | Name of the Material | Qty. | M. Wt. | mM | Mole Ratio |
|---|---|---|---|---|---|
| 1. | Compound of Formula 2(xiii) | 180 mg | 346.15 | 0.52 | 1 |
| 2. | Lithium Hydroxide | 109 mg | 23.95 | 2.6 | 5 |
| 2. | THF/H$_2$O (3:1) | 6 mL | — | — | 33.33 vol. |
| 3. | Ethyl acetate | 2 × 30 mL | 88.11 | — | 2 × 166.67 vol. |
| 4. | Water | 10 mL | 18 | — | 55.55 vol. |
| 5. | Brine | 10 mL | — | — | 55.55 vol. |
| 6. | Na$_2$SO$_4$ | As needed | 142.04 | — | — |

To a solution of compound represented by Formula 2(xiii) (180 mg, 0.52 mmol) in THF/H$_2$O (6 mL, 3:1 ratio), lithium hydroxide (109 mg, 2.6 mmol) was added and stirred at room temperature for 16 h. After completion of starting material, the reaction mixture was quenched with aqueous citric acid solution; pH was adjusted to 4 and extracted with ethyl acetate (30 ml×2). The combined organic extracts were washed with water (10 mL×1), brine solution (10 mL×1) and dried over Na$_2$SO$_4$. The combined organic extracts were evaporated under reduced pressure to obtain the crude product which was purified by column chromatography (100-200 mesh silica gel, the product eluted at 15% EtOAc in hexane) to furnish $^{13}$C DHA (150 mg, 87%) as a pale yellow liquid.

Example 3

Synthesis of a Cyclic Plasmalogen Precursor of Formula A by a 10-Step Synthetic Process In a non-limiting example of a preferred embodiment of the invention, a 10-step synthetic process for production of the cyclic plasmalogen precursor represented by Formula A is now described, wherein R$_1$* is derived from $^{13}$C-iodotridecane, R$_2$* is derived from $^{13}$C-docosahexanoic acid and R$_3$ is hydrogen (See Scheme C). Each of the 10-steps in the process are described below in detail.

Preparation of a Compound of Formula 2—((2,2-dimethyl-1,3-dioxolan-4-yl) methanol)

In the first step the diol of $^{13}$C labeled glycerol was protected as acetonide resulting in production of the compound of Formula 2. The yield of the compound obtained in this reaction step was 78%. The reaction scheme involved in this process is as follows:

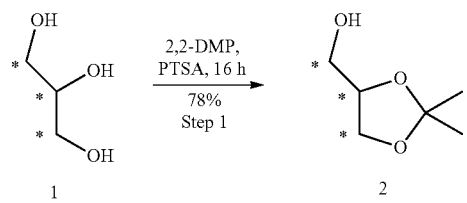

In an exemplary embodiment, the raw materials used for this step are illustrated in Table 1:

TABLE 1

| S. No. | Name of the Material | Qty. | M. Wt. | mmol | Mole Ratio |
|---|---|---|---|---|---|
| 1. | $^{13}$C glycerol | 2 g | 95.19 | 21.01 | 1 |
| 2. | Dichloromethane | 30 mL | 84.93 | — | 15 vol. |
| 3. | PTSA | 181 mg | 172.2 | 0.105 | 0.005 |
| 4. | 2,2-Dimethoxy-propane | 5.6 mL | 104.15 | 46.29 | 2.2 |
| 5. | K$_2$CO$_3$ | | 138.2 | | |
| 6. | DCM | 2 × 50 mL | 84.93 | — | 2 × 25 vol. |

To a solution of $^{13}$C glycerol (2.0 g, 21.01 mmol) in dichloromethane (30 mL), PTSA (181 mg, 0.105 mmol) and 2,2-dimethoxypropane (5.6 mL, 46.29 mmol) were added and the reaction mixture was stirred at room temperature for 16 h. After the completion of starting material, the reaction mixture was quenched with K$_2$CO$_3$, filtered through a Celite™ pad, and washed with CH$_2$Cl$_2$ (2×50 mL). The solvent was evaporated under reduced pressure to obtain the crude product which was purified by column chromatography (100-200 mesh silica gel, eluent 30% EtOAc-hexane) to furnish the compound represented by Formula 2 (2.3 g, 78%) as a pale yellow syrup.

Preparation of a Compound of Formula 3—(4-(allyloxymethyl)-2,2-dimethyl-1,3-dioxolane)

The compound of Formula 2 was coupled to allyl bromide in the presence of NaH to produce a compound of Formula 3. The yield of the compound obtained in this reaction step was 89%. The reaction scheme involved in this process is as follows:

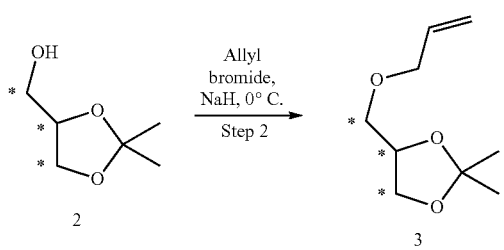

In an exemplary embodiment, the raw materials used for this step are illustrated in Table 2:

TABLE 2

| S. No. | Name of the Material | Qty. | M. Wt. | mmol | Mole Ratio |
|---|---|---|---|---|---|
| 1. | Compound of Formula 2 | 1.5 g | 135.25 | 11.09 | 1 |
| 2. | Allyl Bromide | 1.52 mL | 120.99 | 13.31 | 1.2 |
| 3. | NaH | 887 mg | 24 | 22.1 | 1.99 |
| 4. | THF | 30 mL | 72.11 | — | 20 vol. |
| 5. | Cold water | | 18 | — | |
| 6. | EtOAc | 3 × 50 mL | 88.11 | — | 3 × 33.33 vol. |
| 7. | Water | 15 mL | 18 | — | 10 vol. |
| 8. | Brine | 10 mL | — | — | 6.67 vol. |
| 9. | Na$_2$SO$_4$ | As needed | 142.02 | — | — |

To an ice cold suspension of NaH (887 mg, 22.1 mmol) in THF (30 mL), compound of Formula 2 (1.5 g, 11.09 mmol), allyl bromide (1.52 mL, 13.31 mmol) were sequentially added at 0° C. and stirred at room temperature for 10 h. After completion of starting material, the reaction mixture was quenched with ice cold water (20 mL) and extracted with EtOAc (50 mL×3), washed with H$_2$O (15 mL×1), brine solution (10 mL×1) and dried over anhy. Na$_2$SO$_4$. The combined organic extracts were evaporated under reduced pressure to furnish the compound of Formula 3 (1.7 g, 89%) as a pale yellow liquid which was carried to the next step without further purification.

Preparation of a Compound of Formula 4—(3-(allyloxy) propane-1,2-diol)

The compound of Formula 3 obtained above was deprotected to obtain a compound represented with Formula 4. The reaction scheme involved in this process is as follows:

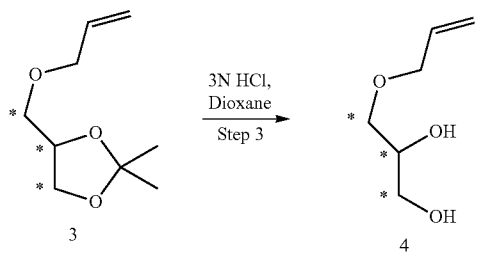

In an exemplary embodiment, the raw materials used for this step are illustrated in Table 3:

TABLE 3

| S. No. | Name of the Material | Qty. | M. Wt. | mmol | Mole Ratio |
|---|---|---|---|---|---|
| 1. | Compound of Formula 3 | 1.7 g | 175.25 | 9.70 | 1 |
| 2. | 1,4-dioxane | 7 mL | 88.11 | — | 4.11 vol. |
| 3. | 3N HCl | 15 mL | 36.5 | — | 8.82 vol. |

To a solution of compound of Formula 3 (1.7 g, 9.70 mmol) in 1,4-dioxane (7 mL), 3N HCl (15 mL) was added and stirred at 80° C. for 3 h. After completion of starting material, solvent was removed by distillation to furnish the compound of Formula 4 (1.3 g, crude) as a brown liquid, which was carried to the next step without further purification.

Preparation of a Compound of Formula 5—(5-(allyloxymethyl)-2,2,3,3,8,8,9,9-octamethyl-4,7-dioxa-3,8-disiladecane)

The diol of the compound of Formula 4 obtained above was protected as a TBDMS ether to obtain the compound represented by Formula 5. The yield of the compound obtained in this reaction step was 71%. The reaction scheme involved in this process is as follows:

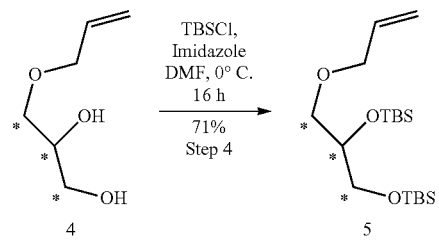

In an exemplary embodiment, the raw materials used for this step are illustrated in Table 4:

TABLE 4

| S. No. | Name of the Material | Qty. | M. Wt. | mmol | Mole Ratio |
|---|---|---|---|---|---|
| 1. | Compound of Formula 4 | 1.3 g | 135.27 | 9.61 | 1 |
| 2. | DMF | 10 mL | 73.09 | — | 3.22 vol. |
| 3. | Imidazole | 1.96 g | 68.05 | 28.8 | 3 |
| 4. | TBDMSCl | 4.34 g | 150.72 | 28.8 | 3 |
| 5. | DMF | 5 mL | 73.09 | — | 3.8 vol. |
| 6. | EtOAc | 4 × 100 mL | 88.11 | — | 4 × 76.92 vol. |
| 7. | Water | 2 × 100 mL | 18 | — | 2 × 76.92 vol. |
| 8. | Brine | 100 mL | — | — | 76.92 vol. |
| 9. | Na$_2$SO$_4$ | As needed | 142.02 | — | — |

To a solution of the compound of Formula 4 (1.3 g, 9.61 mmol) in DMF (10 mL), imidazole (1.96 g, 28.8 mmol) and TBDMSCl (4.34 g, 28.8 mmol) in DMF (5 mL) were added sequentially at 0° C. and stirred at room temperature for 16 h. After completion of starting material, the reaction mixture was extracted with EtOAc (100 mL×4), washed with water (100 mL×2), brine (100 mL×1) and dried over anhy. Na$_2$SO$_4$. The combined organic extracts were evaporated under reduced pressure to obtain the crude product which was purified by column chromatography (100-200 mesh silica gel, eluent 10% EtOAc-hexane) to furnish the compound of Formula 5 (2.4 g, 71%) as a pale yellow liquid.

Preparation of a Compound of Formula 6—((Z)-5-((hexadec-1-enyloxy)methyl)-2,2,3,3,8,8,9,9-octamethyl-4,7-dioxa-3,8-disiladecane)

The compound represented by Formula 5 was reacted with $^{13}$C labeled iodotridecane in the presence of sec-BuLi to produce a compound represented by Formula 6. The yield of the compound obtained in this reaction step was 33%. The reaction scheme involved in this process is as follows:

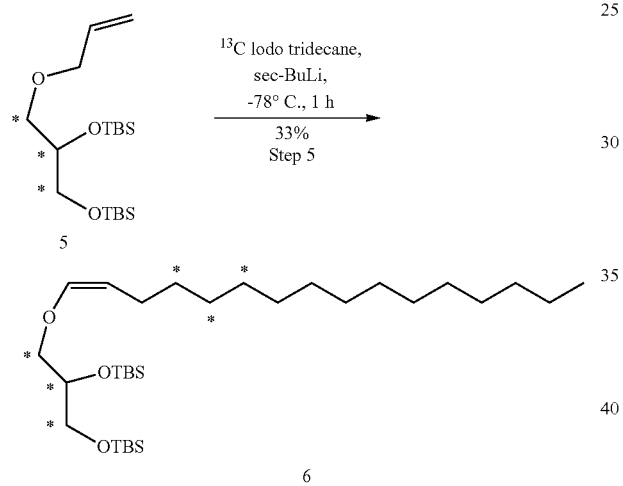

In an exemplary embodiment, the raw materials used for this step are illustrated in Table 5:

TABLE 5

| S. No. | Name of the Material | Qty. | M. Wt. | mmol | Mole Ratio | |
|---|---|---|---|---|---|---|
| 1. | Compound of Formula 5 | 1.06 g | 363.01 | 2.92 | 1 | |
| 2. | THF | 10 mL | 72.11 | — | 9.43 | vol. |
| 3. | Sec-BuLi | 2.71 mL | 64.06 | 3.80 | 1.3 | |
| 4. | $^{13}$C labeled iodotridecane | 1.009 g | 313.35 | 3.22 | 1.1 | |
| 5. | THF | 5 mL | 72.11 | — | 4.72 | vol. |
| 6. | EtOAc | 2 × 100 mL | 88.11 | — | 2 × 94.34 | vol. |
| 8. | Brine | 50 mL | — | — | 47.17 | vol. |
| 9. | Na$_2$SO$_4$ | As needed | 142.02 | — | — | |

To a solution of the compound of Formula 5 (1.06 g, 2.92 mmol) in THF (10 mL), Sec-BuLi (2.71 mL, 3.80 mmol) was added drop wise at −78° C. and stirred for 5 min and $^{13}$C labeled iodotridecane (1.009 g, 3.22 mmol) (synthesized in house) in THF (5 mL) was added drop wise and stirred at room temperature for 1 h. After completion of the reaction, the reaction mixture was quenched with ice cold water and extracted with EtOAc (100 mL×2) and washed with brine (50 mL×1) and dried over anhy. Na$_2$SO$_4$. The combined organic extracts were evaporated under reduced pressure to obtain the crude product which was purified by column chromatography (100-200 mesh silica gel, eluent 20% DCM-hexane) to furnish the compound of Formula 6 (0.54 g, 33%) as a colorless liquid.

Preparation of a Compound of Formula 7 ((Z)-3-(hexadec-1-enyloxy) propane-1,2-diol)

The compound represented by Formula 6 obtained above was deprotected of TDBMS ether to produce a compound of Formula 7. The yield of the compound obtained in this reaction step was 73%. The reaction scheme involved in this process is as follows:

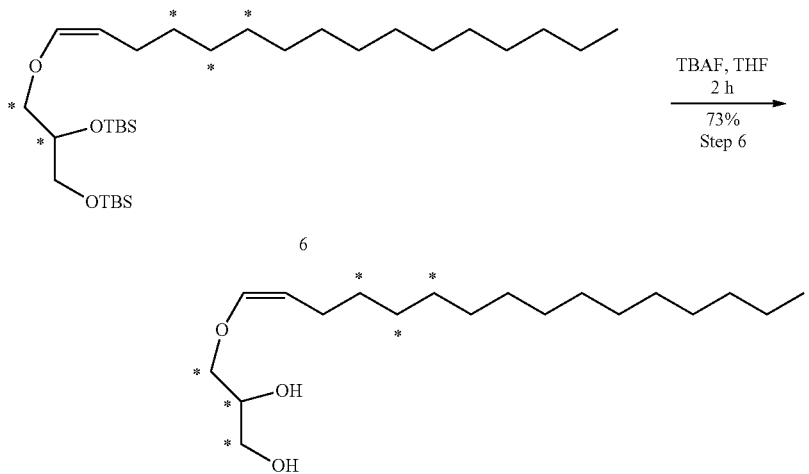

In an exemplary embodiment, the raw materials used for this step are illustrated in Table 6:

TABLE 6

| S. No. | Name of the Material | Qty. | M. Wt. | mmol | Mole Ratio |
|---|---|---|---|---|---|
| 1. | Compound of Formula 6 | 0.54 g | 545.54 | 0.99 | 1 |
| 2. | THF | 5 mL | 72.11 | — | 9.25 vol. |
| 3. | TBAF | 3.97 mL | 261.46 | 3.97 | 4.01 |
| 4. | EtOAc | 2 × 25 mL | 88.11 | — | 2 × 46.29 vol. |
| 5. | Water | 2 × 50 mL | 18 | — | 2 × 92.59 vol. |
| 6. | Brine | 50 mL | — | — | 92.59 vol. |
| 7. | Na$_2$SO$_4$ | As needed | 142.02 | — | — |

To an ice cold solution of the compound of Formula 6 (0.54 g, 0.99 mmol) in THF (5 mL), TBAF (3.97 mL, 3.97 mmol) was added drop wise and stirred at room temperature for 2 h. After completion of starting material, the reaction mixture was extracted with ethyl acetate (25 mL×2), washed with water (50 mL×2), brine (50 mL×1) and dried over anhy. Na$_2$SO$_4$. The combined organic extracts were evaporated under reduced pressure to obtain the crude product which was purified by column chromatography (100-200 mesh silica gel, eluent 40% EtOAc-hexane) to furnish the compound of Formula 7 (233 mg, 73%) as an off white solid.

Preparation of a Compound of Formula 8 ((Z)-1-(tert-butyldimethylsilyloxy)-3-(hexadec-1-enyloxy) propan-2-ol)

Primary alcohol present in the compound represented by Formula 7 was protected with TDBMS to obtain a compound represented by Formula 8. The yield of the compound obtained in this reaction step was 55%. The reaction scheme involved in this process is as follows:

In an exemplary embodiment, the raw materials used for this step are illustrated in Table 7:

TABLE 7

| S. No. | Name of the Material | Qty. | M. Wt. | mmol | Mole Ratio |
|---|---|---|---|---|---|
| 1. | Compound of Formula 7 | 400 mg | 322.58 | 1.24 | 1 |
| 2. | DCM | 5 mL | 84.93 | — | 12.5 vol. |
| 3. | TEA | 0.43 mL | 101.19 | 3.12 | 2.51 |
| 4. | DMAP | 153 mg | 122.17 | 1.24 | 1 |
| 5. | TBDMSCl | 207 mg | 143.06 | 1.37 | 1.1 |
| 6. | Dichloromethane | 2 × 20 mL | 84.93 | — | 2 × 50 vol. |
| 7. | Water | 2 × 15 mL | 18 | — | 2 × 37.5 vol. |
| 8. | Brine | 2 × 10 mL | — | — | 2 × 25 vol. |
| 9. | Na$_2$SO$_4$ | As needed | 142.02 | — | — |

To an ice cold solution of the compound of Formula 7 (400 mg, 1.24 mmol) in DCM (5 mL), TEA (0.43 mL, 3.12 mmol), DMAP (153 mg, 1.24 mmol) and TBDMSCl (207 mg, 1.37 mmol) were added sequentially and stirred at room temperature for 16 h. After the completion of starting material, the reaction mixture was extracted with dichloromethane (20 mL×2), washed with water (15 mL×2), brine (10 mL×2) and dried over anhy. Na$_2$SO$_4$. The combined organic extracts were evaporated under reduced pressure to obtain the crude product which was purified by column chromatography (100-200 mesh silica gel, eluent 5% EtOAc-hexane) to furnish the compound of Formula 8 (300 mg, 55%) as a colorless liquid.

Preparation of a Compound of Formula 9 ((4Z,7Z,10Z,13Z,16Z,19Z)-1-(tert-butyldimethylsilyloxy)-3-((Z)-hexadec-1-enyloxy) propan-2-yl docosa-4,7,10,13,16,19-hexaenoate)

$^{13}$C labeled DHA was esterified at the sn2 position of the compound represented by Formula 8 in the presence of EDC.HCL/DMAP to produce a compound represented by Formula 9. The yield of the compound obtained in this reaction step was 77%. The reaction scheme involved in this process is as follows:

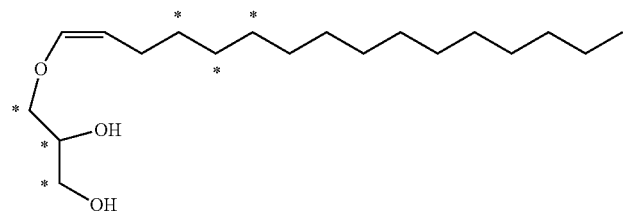

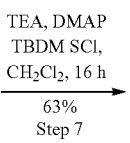

TEA, DMAP
TBDM SCl,
CH$_2$Cl$_2$, 16 h
———————→
63%
Step 7

7

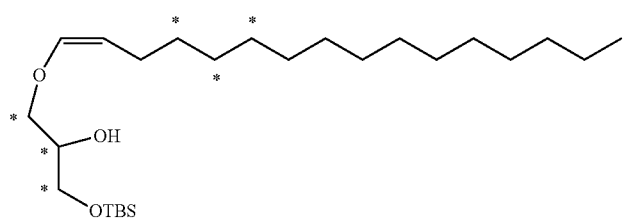

8

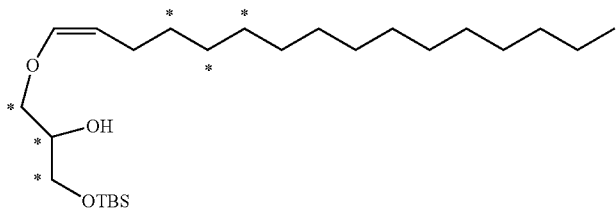

8

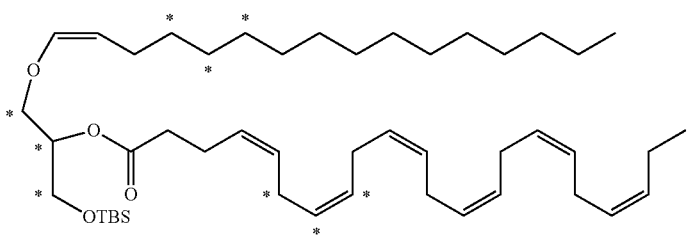

9

In an exemplary embodiment, the raw materials used for this step are illustrated in Table 8:

TABLE 8

| S. No. | Name of the Material | Qty. | | M. Wt. | mmol | Mole Ratio | |
|---|---|---|---|---|---|---|---|
| 1. | Compound of Formula 8 | 150 | mg | 441.17 | 0.34 | 1 | |
| 2. | DCM | 10 | mL | 84.93 | — | 66.67 | vol. |
| 3. | $^{13}$C labeled DHA | 125 | mg | 337.83 | 0.37 | 1.08 | |
| 4. | EDC•HCl | 79 | mg | 191.7 | 0.41 | 1.2 | |
| 5. | DMAP | 4 | mg | 122.17 | 0.03 | 0.09 | |
| 6. | Dichloromethane | 2 × 25 | mL | 84.93 | — | 2 × 166.67 | vol. |
| 7. | Water | 2 × 25 | mL | 18 | — | 2 × 166.67 | vol. |
| 8. | Brine | 50 | mL | — | — | 333.33 | vol. |
| 9. | Na$_2$SO$_4$ | As needed | | 142.02 | — | — | |

To an ice cold solution of the compound of Formula 8 (150 mg, 0.34 mmol) in DCM (10 mL), $^{13}$C DHA (synthesized in house) (125 mg, 0.37 mmol), EDC.HCl (79 mg, 0.41 mmol) and DMAP (4 mg, 0.03 mmol) were added sequentially and stirred at room temperature for 16 h. After completion of starting materials, the reaction mixture was extracted with DCM (25 mL×2) and washed with water (25 mL×2), brine (50 mL×1) and dried over anhy. Na$_2$SO$_4$. The combined organic extracts were evaporated under reduced pressure to obtain the crude product which was purified by column chromatography (100-200 mesh silica gel, eluent 5% EtOAc-hexane) to furnish the compound of Formula 9 (0.2 gm, 77%) as a pale yellow liquid.

Preparation of a Compound of Formula 10—((4Z, 7Z,10Z,13Z,16Z,19Z)-1-((Z)-hexadec-1-enyloxy)-3-hydroxypropan-2-yl 13C docosa-4,7,10,13,16,19-hexaenoate)

The compound represented by Formula 9 was deprotected in the presence of excess AcOH to produce a compound as represented by Formula 10. The yield of the compound obtained in this reaction step was 59%. The reaction scheme involved in this process is as follows:

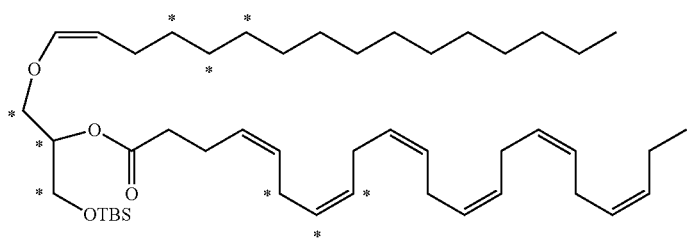

9

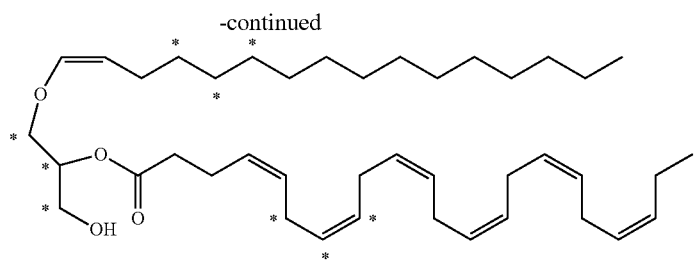

10

In an exemplary embodiment, the raw materials used for this step are illustrated in Table 9:

TABLE 9

| S. No. | Name of the Material | Qty. | M. Wt. | mmol | Mole Ratio |
|---|---|---|---|---|---|
| 1. | Compound of Formula 9 | 0.2 g | 769.23 | 0.26 | 1 |
| 2. | THF | 10 mL | 72.11 | — | 50 vol. |
| 3. | AcOH | 0.16 mL | 60.05 | 2.67 | 10.27 |
| 4. | TBAF | 0.8 mL | 261.46 | 0.80 | 3.07 |
| 5. | EtOAc | 2 × 25 mL | 88.11 | — | 2 × 125 vol. |
| 6. | Water | 2 × 25 mL | 18 | — | 2 × 125 vol. |
| 7. | NaHCO₃ | 25 mL | 84.01 | — | 125 vol. |
| 8. | Brine | 25 mL | — | — | 125 vol. |
| 9. | Na₂SO₄ | As needed | 142.02 | — | — |

To an ice cold solution of the compound of Formula 9 (0.2 g, 0.26 mmol) in THF (10 mL), AcOH (0.16 mL, 2.67 mmol) and TBAF (0.8 mL, 0.80 mmol) were added and stirred at room temperature for 3 h. After the completion of starting materials, the reaction mixture was extracted with EtOAc (25 mL×2) and washed with water (25 mL×2), NaHCO₃ (25 mL×1), brine (25 mL×1) and dried over anhy. Na₂SO₄. The combined organic extracts were evaporated under reduced pressure to obtain the crude product which was purified by column chromatography (100-200 mesh silica gel, eluent 20% EtOAc-hexane) to furnish the compound of Formula 10 (0.1 gm, 59%) as a pale yellow liquid.

Preparation of a Compound of Formula A

A cyclic phosphoethanolamine group was added to the compound represented by Formula 10 to produce a compound as represented by Formula A, using a two step protocol, wherein POCl₃ was added to the compound represented by Formula 9 to produce a dichlorophosphate intermediate, which was quenched with ethanolamine to give the cyclic phosphoethanolamine. The yield of the compound obtained in this reaction step was 44%. The reaction scheme involved in this process is as follows:

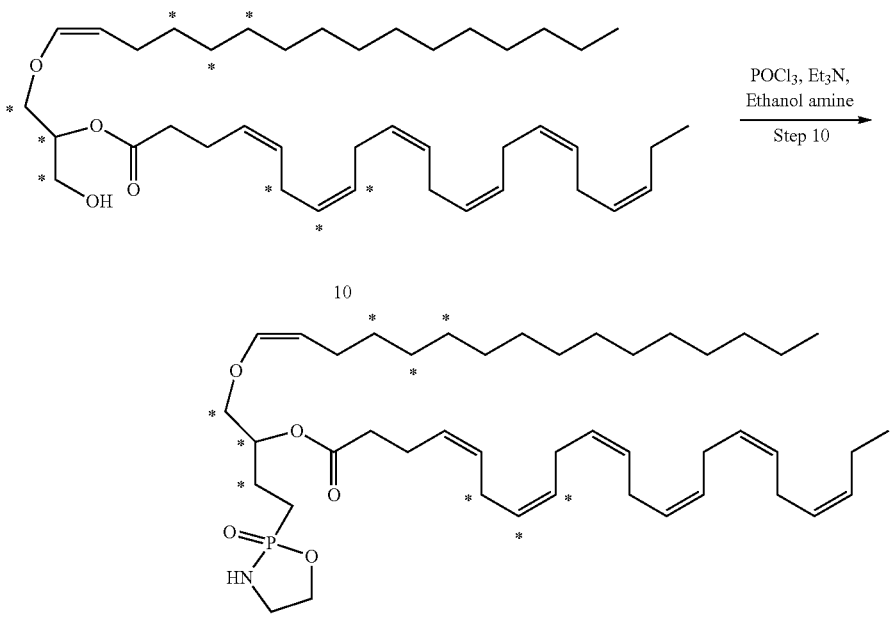

In an exemplary embodiment, the raw materials used for this step are illustrated in Table 10:

TABLE 10

| S. No. | Name of the Material | Qty. | M. Wt. | mmol | Mole Ratio |
|---|---|---|---|---|---|
| 1. | Compound of Formula 10 | 60 mg | 666.67 | 0.09 | 1 |
| 2. | POCl$_3$ | 0.02 mL | 153.33 | 0.28 | 3.11 |
| 3. | Hexane | 2 mL | 86.18 | — | 33.3 vol. |
| 4. | TEA | 0.12 mL | 101.19 | 0.90 | 10 |
| 5. | Trichloroethylene | 4 mL | 131.39 | — | 66.67 vol. |
| 6. | Toluene | 10 mL | 92.14 | — | 166.67 vol. |
| 7. | THF | 6 mL | 72.11 | — | 100 vol. |
| 8. | Ethanolamine | 17 mg | 61.08 | 0.28 | 3.11 |
| 9. | TEA | 0.5 mL | 101.19 | 3.6 | 40 |
| 10. | THF | 5 mL | 72.11 | — | 83.33 vol. |
| 11. | EtOAc | 10 mL | 88.11 | — | 167.67 vol. |

To an ice cold solution of POCl$_3$ (0.02 mL, 0.28 mmol) in hexane (2 mL), TEA (0.12 mL, 0.90 mmol) and the compound of Formula 10 (60 mg, 0.09 mmol) in trichloroethylene (4 mL) were added at 0° C. drop wise and stirred at 0° C. for 30 min and 1 h at room temperature. The reaction mixture was filtered through small a Celite™ pad, washed with toluene (10 mL) and the filtrate was evaporated under reduced pressure.

The crude material obtained was dissolved in THF (6 mL) ethanolamine (17 mg, 0.28 mmol) and TEA (0.5 mL, 3.6 mmol) in THF (5 mL) were added at 0° C. drop wise to the reaction mixture and stirred at room temperature for 30 min. The reaction mixture was filtered through a Celite™ pad and washed with EtOAc (10 mL). The combined organic extracts were evaporated under reduced pressure to obtain the crude product which was purified by column chromatography (100-200 mesh silica gel, eluent 60% EtOAc-hexane) to furnish the compound of Formula A (26 mg, 44%) as a pale yellow liquid.

Example 4

Conversion of a Compound of Formula A to a Compound of Formula B

In an example of a preferred embodiment of the invention described herein, a one step synthetic process is described below in detail for conversion of a compound represented by Formula A as obtained above to a compound represented by Formula B.

Preparation of a Compound of Formula B

A compound of Formula A comprising a cyclic phosphoethanolamine was converted to a compound represented by Formula B in the presence of THF and H$_2$O. The reaction scheme involved in this process is as follows:

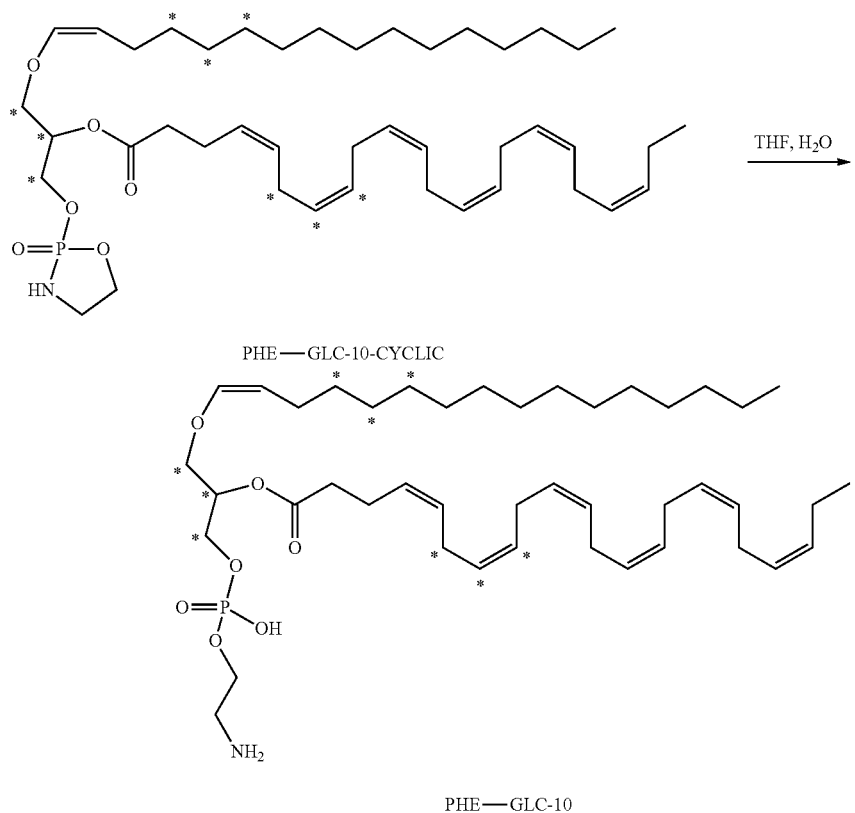

In an exemplary embodiment, the raw materials used for this step are illustrated in Table 11:

TABLE 11

| S. No. | Name of the Material | Qty. | M. Wt. | mmol | Mole Ratio |
|---|---|---|---|---|---|
| 1. | Compound of Formula A | 60 mg | 636.36 | 0.09 | 1 |
| 2. | THF | 1 mL | 72.11 | — | 16.67 vol. |
| 3. | Water | 0.5 mL | 18 | — | 8.33 vol. |

The compound of Formula A was dissolved in tetrahydrofuran (1 mL) and 0.5 mL of water was added. The solution was stirred for 3 h to give the compound of Formula B.

The preferred embodiments of the invention described above are merely exemplary of the invention, which can be embodied in various forms. Therefore, specific details relating to the reagents and reaction conditions disclosed herein are not to be interpreted as limiting, but merely as an example. It will also be apparent to a person skilled in the art that a number of variations and modifications can be made without departing from the scope of the invention as defined in the claims.

What is claimed is:

1. A process of preparing a compound represented by Formula A

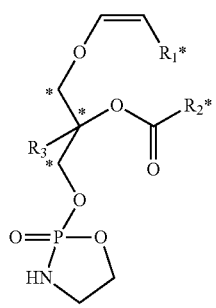

Formula A wherein the compound is $^{13}C$ labeled at one or more carbon atoms marked with an asterisk, $R_1^*$ and $R_2^*$ are the same or different $^{13}C$ labeled saturated, unsaturated, or polyunsaturated $C_1$-$C_{28}$ hydrocarbon chains comprising at least one $^{13}C$ labeled carbon atom, and optionally derived from fatty acids; and $R_3$ is hydrogen or a $C_1$-$C_3$ alkyl group, the process comprising:

a) protecting the diol present in $^{13}C$ labeled glycerol of Formula 1:

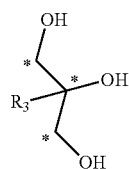

Formula 1 by reaction with dimethoxypropane to obtain a solketal represented by the compound of Formula 2:

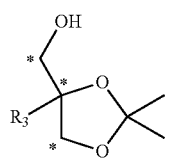

Formula 2 b) coupling the primary alcohol in the compound of Formula 2 with an allyl halide to obtain a compound represented by Formula 3:

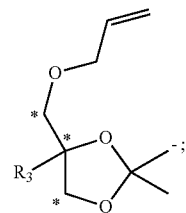

Formula 3 c) deprotecting the ketal present in the compound represented by Formula 3 to obtain a compound represented by Formula 4

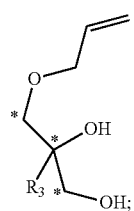

Formula 4 d) protecting the diol present in the compound represented by Formula 4 using a protecting agent to obtain a compound represented by Formula (v):

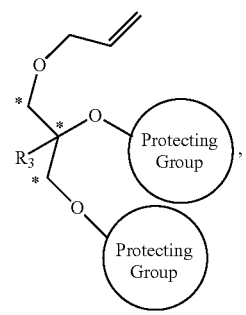

Formula (v)

e) reacting a $^{13}C$ labeled haloalkane as represented by X—$R_1^*$ with the compound represented by Formula (v) to obtain a compound represented by Formula (vi)

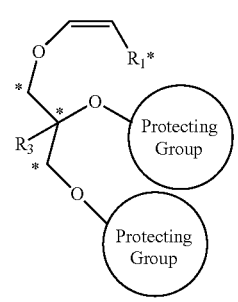

Formula (vi)

wherein $R_1^*$ is as defined above and X is a halogen, f) deprotecting the ether groups present in the compound represented by Formula (vi) to obtain a compound represented by Formula 7

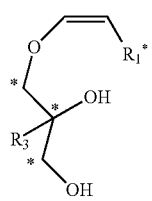

Formula 7 g) protecting the primary alcohol present in the compound represented by Formula 7 using a protecting agent to obtain a compound represented by Formula (viii)

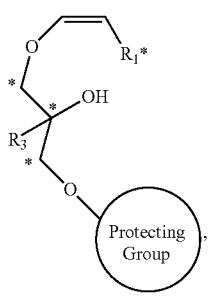

Formula (viii)

h) esterifying a $^{13}C$ labeled fatty acid as represented by $R_2^*$—COOH to the compound represented by Formula (viii) to obtain a compound represented by Formula (ix):

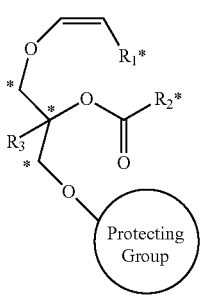

Formula (ix)

wherein $R_2^*$ is as defined above, i) deprotecting the ether present in the compound represented by Formula (ix) to yield a compound represented by Formula 10

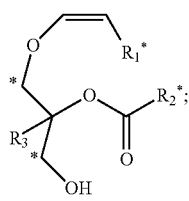

Formula 10 and j) reacting $POCl_3$ with the compound represented by Formula 10, ethanolamine, and triethanolamine (TEA) to yield the compound represented by Formula A.

2. The process as claimed in claim 1 wherein $R_1^*$, $R_2^*$ or both $R_1^*$ and $R_2^*$ are $C_1$-$C_{28}$ alkyl chains comprising up to 6 double bonds.

3. The process as claimed in claim 1 wherein $R_1^*$ is a $C_1$-$C_{20}$ alkyl group.

4. The process as claimed in claim 1 wherein $R_2^*$ is a C2-C28 alkenyl group with 1 to 6 double bonds.

5. The process as claimed in claim 1 wherein $R_3$ is hydrogen.

6. The process as claimed in claim 1 wherein the allyl halide is allyl bromide.

7. The process as claimed in claim 1 wherein the diol present in the compound represented by Formula 4 is protected with a tert-butyldimethylsilyl (TBS) group.

8. The process as claimed in claim 1 wherein X in $XR_1^*$ is Cl, Br, F or I.

9. The process as claimed in claim 8 wherein X in $XR_1^*$ is I.

10. The process as claimed in claim 1 wherein the primary alcohol present in the compound represented by Formula 7 is protected with a tert-butyldimethylsilyl (TBS) group.

11. The process as claimed in claim 1 wherein the $^{13}C$ labeled haloalkane as represented by X—$R_1^*$ in step (e) is $^{13}C$-iodotridecane.

12. The process as claimed in claim 11 wherein the is $^{13}C$-iodotridecane is chemically synthesized.

13. The process as claimed in claim 1 wherein the $^{13}C$ labeled fatty acid as represented by $R_2^*$—COOH in step (h) is $^{13}C$-docosahexaenoic acid ($^{13}C$-DHA).

14. The process as claimed in claim 13 wherein the $^{13}C$-DHA is chemically synthesized.

15. The process as claimed in claim 1, wherein the protecting reaction of step (a) is carried out in the presence of dimethoxy propane and p-toluenesulfonic acid (PTSA).

16. The process as claimed in claim 15, wherein the protecting reaction of step (a) is carried out at about room temperature.

17. The process as claimed in claim 1, wherein the coupling reaction of step (b) is carried out in the presence of NaH, tetrahydrofuran (THF) and allyl bromide.

18. The process as claimed in claim 17, wherein the coupling reaction of step (b) is carried out at a temperature of between about 0° C. to about room temperature.

19. The process as claimed in claim 1, wherein the deprotecting reaction of step (c) is conducted under acidic conditions in the presence of HCl.

20. The process as claimed in claim 19, wherein the deprotecting reaction of step (c) is carried out at a temperature of about 80° C.

21. The process as claimed in claim 1, wherein the protection reaction of step (d) comprises reacting the compound represented by Formula 4 with a tert-butyldimethylsilyl chloride (TBDMSCl) in the presence of DMF and Imidazole.

22. The process as claimed in claim 21, wherein the protection reaction of step (d) is carried out at a temperature of between about 0° C. to about room temperature.

23. The process as claimed in claim 1, wherein the step (e) comprises reacting a haloalkane dissolved in THF with the compound represented by Formula (v) in the presence of tetrahydrofuran (THF) and Sec-BuLi.

24. The process as claimed in claim 23, wherein the step (e) is carried out at a temperature of between about −78° C. to about room temperature.

25. The process as claimed in claim 24, wherein the haloalkane is $^{13}C$-iodotridecane.

26. The process as claimed in claim 25, wherein the compound formed in step (e) is an α alkylated compound as represented by Formula (vi).

27. The process as claimed in claim 1, wherein the deprotection reaction of step (f) is carried out in presence of tetrahydrofuran (THF) and tetra-n-butylammonium fluoride (TBAF).

28. The process as claimed in claim 27, wherein the deprotection reaction of step (f) is carried out at a temperature of between about 0° C. to about room temperature.

29. The process as claimed in claim 1, wherein the protection reaction of step (g) comprises reacting tert-butyldimethylsilyl chloride (TBDMSCl) with the compound represented by Formula 7 in the presence of dichloromethane (DCM), DEA and 4-dimethylaminopyridine (DMAP).

30. The process as claimed in claim 29, wherein the protection reaction of step (g) is carried out at a temperature of between about 0° C. to about room temperature.

31. The process as claimed in claim 1, wherein the esterification reaction of step (h) is carried out in the presence of dichloromethane (DCM), 1-ethyl-3-(3-dimethyllaminopropyl) carbodiimide hydrochloride (EDC.HCl) and 4-dimethylaminopyridine (DMAP).

32. The process as claimed in claim 31, wherein the esterification reaction of step (h) is carried out at a temperature of between about 0° C. to about room temperature.

33. The process as claimed in claim 32, wherein the $^{13}$C labeled fatty acid is $^{13}$C-docosahexaenoic acid ($^{13}$C-DHA).

34. The process as claimed in claim 1, wherein the deprotection reaction of step (i) is carried out in the presence of tetrahydrofuran (THF), AcOH and tetra-n-butylammonium fluoride (TBAF).

35. The process as claimed in claim 34, wherein the deprotection reaction of step (i) is carried out at a temperature of between about 0° C. to about room temperature.

36. The process as claimed in claim 1, wherein the step (j) comprises:
   a) reacting POCl$_3$ with the compound represented by Formula 10 dissolved in trichloroethylene in the presence of hexane and triethanolamine (TEA) to obtain a crude material;
   b) dissolving the crude material in tetrahydrofuran (THF) forming a reaction mixture; and
   c) adding ethanolamine and TEA in THF to the reaction mixture to yield a compound represented by Formula A.

37. The process as claimed in claim 1, wherein the step (j) is carried out at a temperature of between about 0° C. to about room temperature.

38. The process as claimed in claim 1, wherein the compound represented by Formula A is:

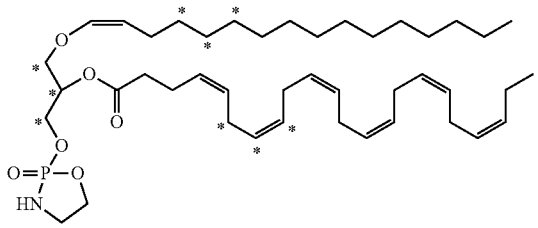

Formula A'

39. A process of converting a compound represented by Formula A:

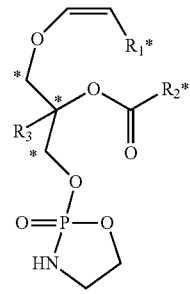

Formula A wherein the compound is $^{13}$C labeled at one or more carbon atoms marked with an asterisk, R$_1$* and R$_2$* are the same or different $^{13}$C labeled saturated, unsaturated, or polyunsaturated C$_1$-C$_{28}$ hydrocarbon chains comprising at least one $^{13}$C labeled carbon atom, and optionally derived from fatty acids; and R$_3$ is hydrogen or a C$_1$-C$_3$ alkyl group, the process comprising converting the compound represented by Formula A to a compound represented by Formula B:

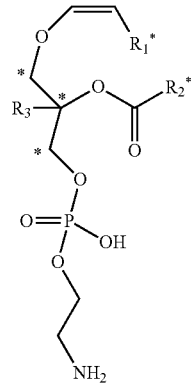

Formula B the conversion process being carried out in the presence of tetrahydrofuran (THF) and H$_2$O.

40. The process as claimed in claim 39, wherein the compound represented by Formula A is

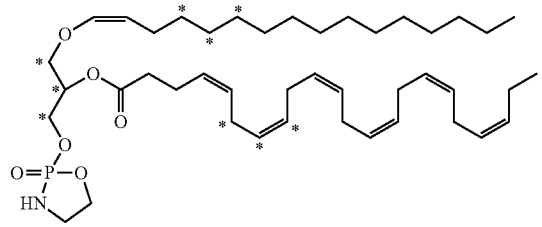

Formula A'

41. The compound of Formula A:

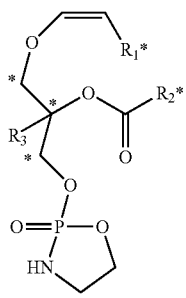

Formula A wherein the compound is $^{13}C$ labeled at one or more carbon atoms marked with an asterisk, $R_1^*$ and $R_2^*$ are the same or different $^{13}C$ labeled saturated, unsaturated, or poly-unsaturated $C_1$-$C_{28}$ hydrocarbon chains comprising at least one $^{13}C$ labeled carbon atom, and optionally derived from fatty acids; and $R_3$ is hydrogen or a $C_1$-$C_3$ alkyl group, prepared by the process as claimed in claim 1.

42. The compound of Formula B:

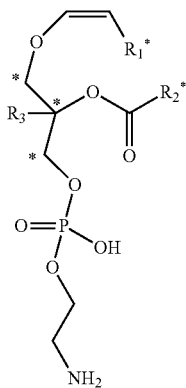

Formula B wherein the compound is $^{13}C$ labeled at one or more carbon atoms marked with an asterisk, $R_1^*$ and $R_2^*$ are the same or different $^{13}C$ labeled saturated, unsaturated, or poly-unsaturated $C_1$-$C_{28}$ hydrocarbon chains comprising at least one $^{13}C$ labeled carbon atom, and optionally derived from fatty acids; and $R_3$ is hydrogen or a $C_1$-$C_3$ alkyl group, the compound of Formula B being prepared by the process of claim 39.

43. A reference marker for use in metabolic studies comprising a compound of Formula B:

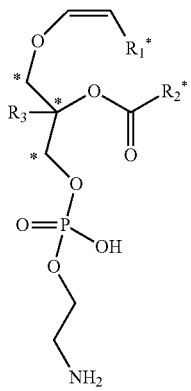

Formula B wherein the compound is $^{13}C$ labeled at one or more carbon atoms marked with an asterisk, $R_1^*$ and $R_2^*$ are the same or different $^{13}C$ labeled saturated, unsaturated, or poly-unsaturated $C_1$-$C_{28}$ hydrocarbon chains comprising at least one $^{13}C$ labeled carbon atom, and optionally derived from fatty acids; and $R_3$ is hydrogen or a $C_1$-$C_3$ alkyl group.

44. The reference marker as claimed in claim 43, wherein the compound represented by Formula B is:

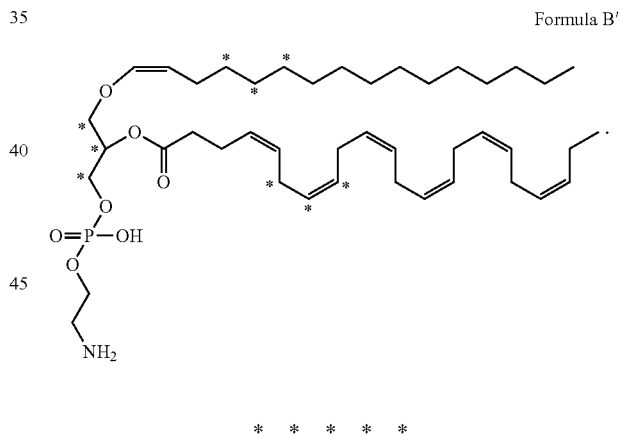

Formula B'

\* \* \* \* \*